(12) United States Patent
Srimohanarajah et al.

(10) Patent No.: US 11,523,871 B2
(45) Date of Patent: Dec. 13, 2022

(54) OPTICAL-BASED INPUT FOR MEDICAL DEVICES

(71) Applicant: SYNAPTIVE MEDICAL INC., Toronto (CA)

(72) Inventors: Kirusha Srimohanarajah, Toronto (CA); Dorothy Lui, Toronto (CA); Gal Sela, Toronto (CA); Stephen Elliott Soman, Toronto (CA); Sepide Movaghati, Toronto (CA)

(73) Assignee: Avidbots Corp, Kitchener (CA)

( * ) Notice: Subject to any disclaimer, the term of this patent is extended or adjusted under 35 U.S.C. 154(b) by 656 days.

(21) Appl. No.: 16/468,191

(22) PCT Filed: Dec. 8, 2016

(86) PCT No.: PCT/CA2016/051440
§ 371 (c)(1),
(2) Date: Jun. 10, 2019

(87) PCT Pub. No.: WO2018/102904
PCT Pub. Date: Jun. 14, 2018

(65) Prior Publication Data
US 2020/0008878 A1 Jan. 9, 2020

(51) Int. Cl.
*A61B 34/20* (2016.01)
*A61B 90/00* (2016.01)
(Continued)

(52) U.S. Cl.
CPC ............ *A61B 34/20* (2016.02); *A61B 34/25* (2016.02); *A61B 90/39* (2016.02);
(Continued)

(58) Field of Classification Search
CPC .......... A61B 34/25; A61B 2017/00207; A61B 34/20; A61B 90/39; A61B 2034/2055;
(Continued)

(56) References Cited

U.S. PATENT DOCUMENTS 7,865,266 B2 1/2011 Moll et al.
2005/0215888 A1* 9/2005 Grimm ................. A61B 90/39
600/426
(Continued)

FOREIGN PATENT DOCUMENTS

WO 2015035057 A1 3/2015

OTHER PUBLICATIONS

International Search Report and Written Opinion issued by the International Searching Authority in relation to corresponding PCT Application No. PCT/CA2016/051440, with dated Aug. 25, 2017, 24 pgs.

*Primary Examiner* — Amelie R Davis

(57) ABSTRACT

A system for adjusting an operating state of a medical electronic device is described. In an aspect, the system includes an optical tracking system configured to detect three or more tracking markers. The system also includes a processor coupled with the optical tracking system. The processor is programmed with instructions which, when executed, configure the processor to: configure an input command by assigning at least one operating state of the medical electronic device to a particular state of at least one of the tracking markers; after receiving a priming command, identify a present state of the tracking markers based on data from the optical tracking system; compare the present state with the particular state assigned to the operating state; and based on the comparison, determine that an input command has been received and adjust the operating state of the medical electronic device to the assigned operating state.

20 Claims, 15 Drawing Sheets

(51) Int. Cl.
*A61B 34/00* (2016.01)
*A61B 17/00* (2006.01)

(52) U.S. Cl.
CPC ............. *A61B 2017/00207* (2013.01); *A61B 2034/2055* (2016.02); *A61B 2034/2068* (2016.02); *A61B 2090/3983* (2016.02)

(58) Field of Classification Search
CPC .... A61B 2034/2068; A61B 2090/3983; G06F 3/005; G06F 3/017; G06F 3/03; G06F 3/0346; G06F 3/03545
See application file for complete search history.

(56) References Cited

U.S. PATENT DOCUMENTS

| | | | |
|---|---|---|---|
| 2007/0016008 A1* | 1/2007 | Schoenefeld | A61B 90/36 600/424 |
| 2007/0073137 A1* | 3/2007 | Schoenefeld | A61B 90/36 600/407 |
| 2011/0118753 A1 | 5/2011 | Itkowitz et al. | |
| 2014/0081455 A1 | 3/2014 | Goldberg et al. | |
| 2014/0125557 A1* | 5/2014 | Issayeva | G06T 19/20 345/8 |
| 2015/0076209 A1 | 3/2015 | Shelton et al. | |
| 2015/0351860 A1 | 12/2015 | Piron et al. | |
| 2016/0367321 A1* | 12/2016 | Daon | A61C 1/082 |

* cited by examiner

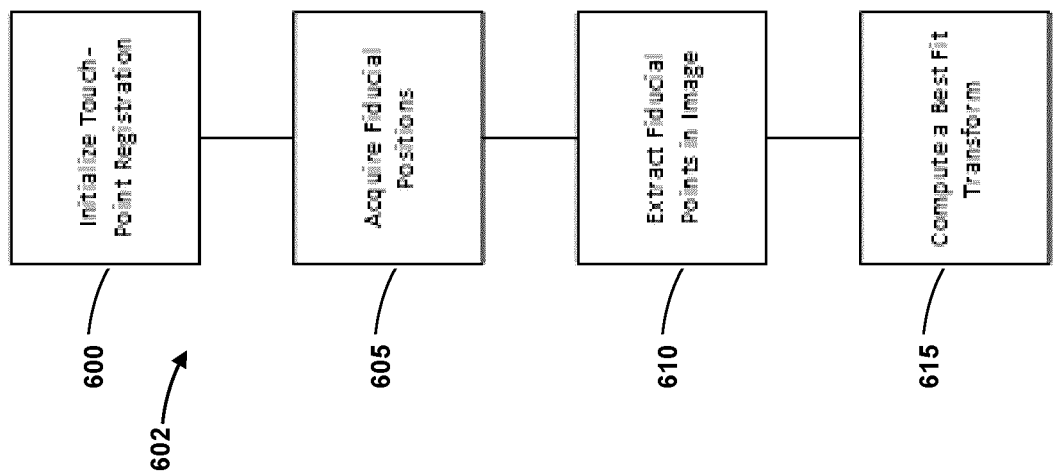
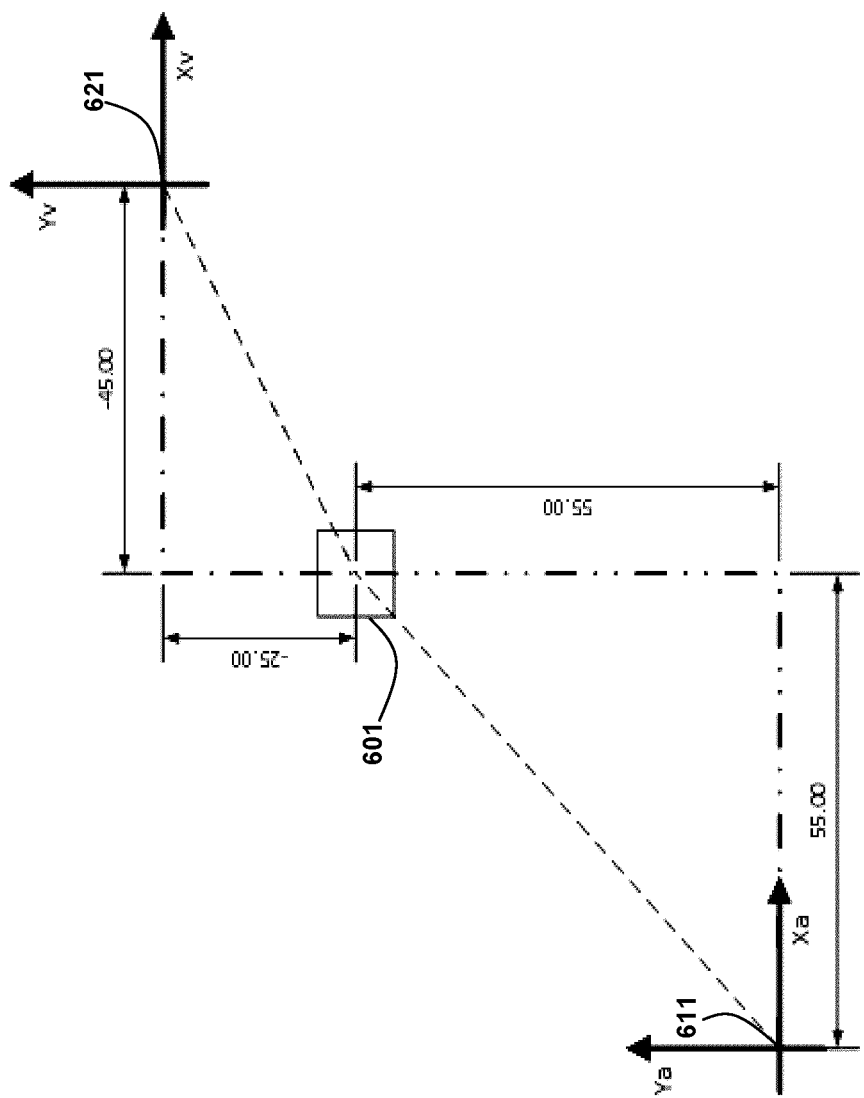
Figure 6

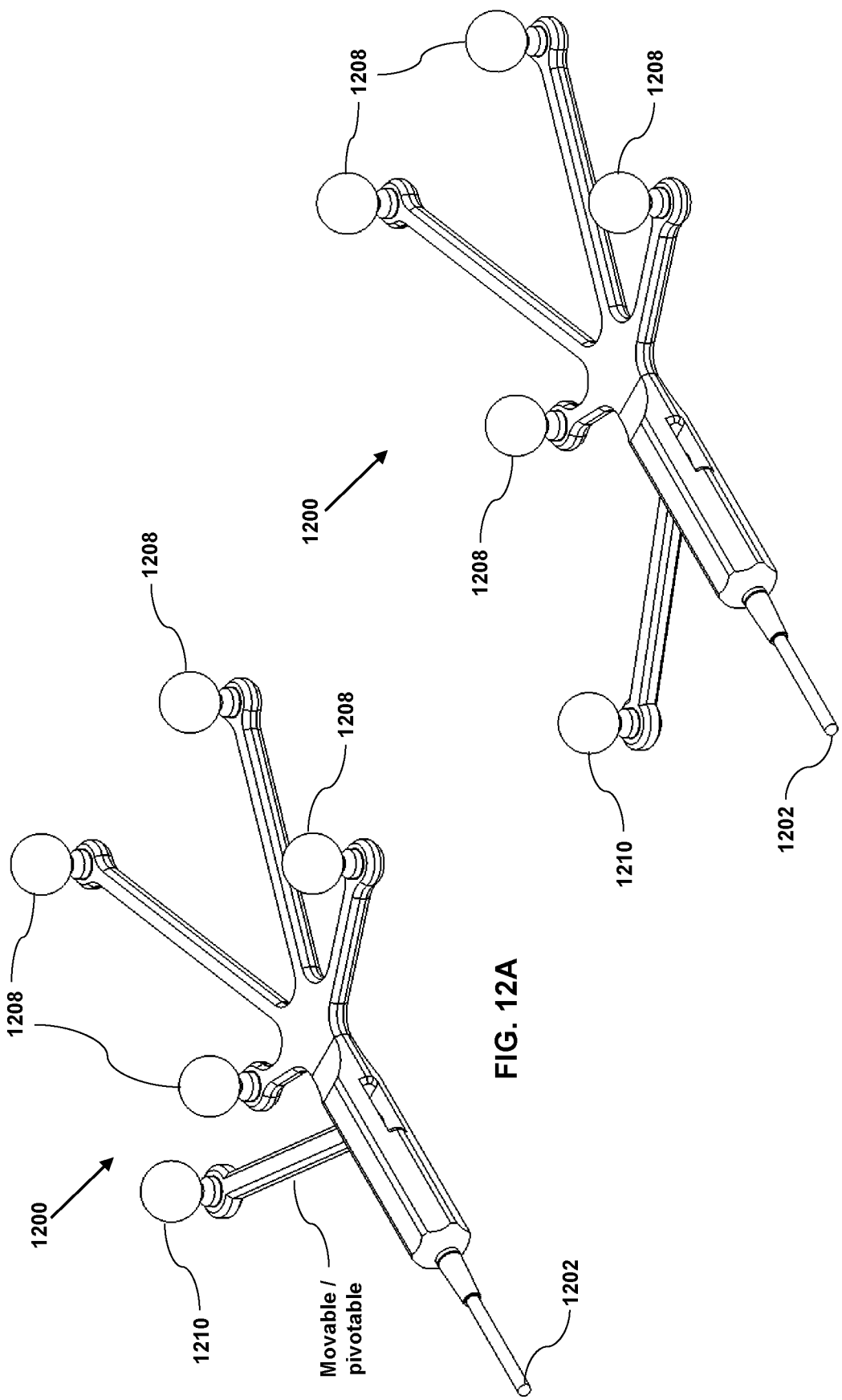

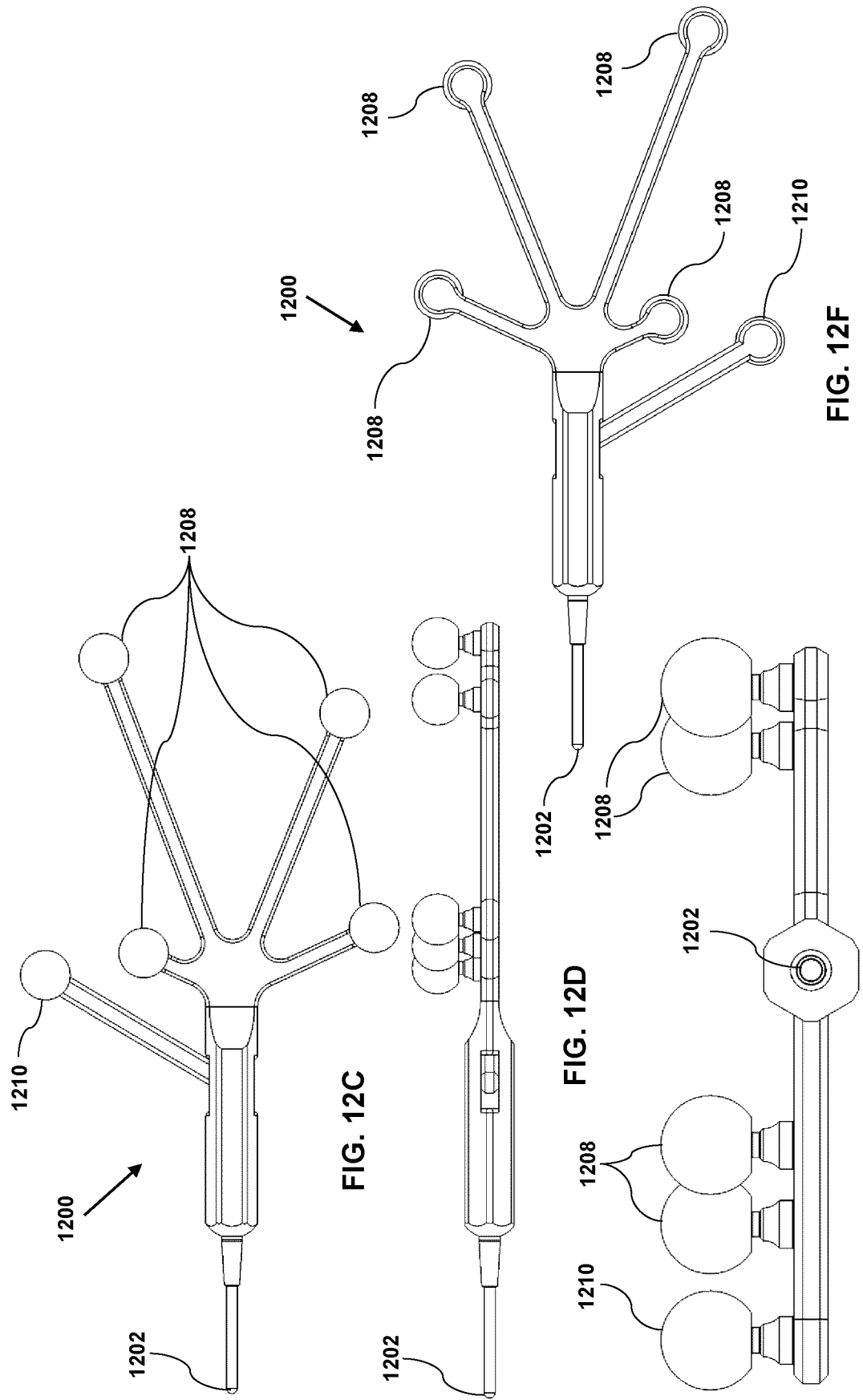

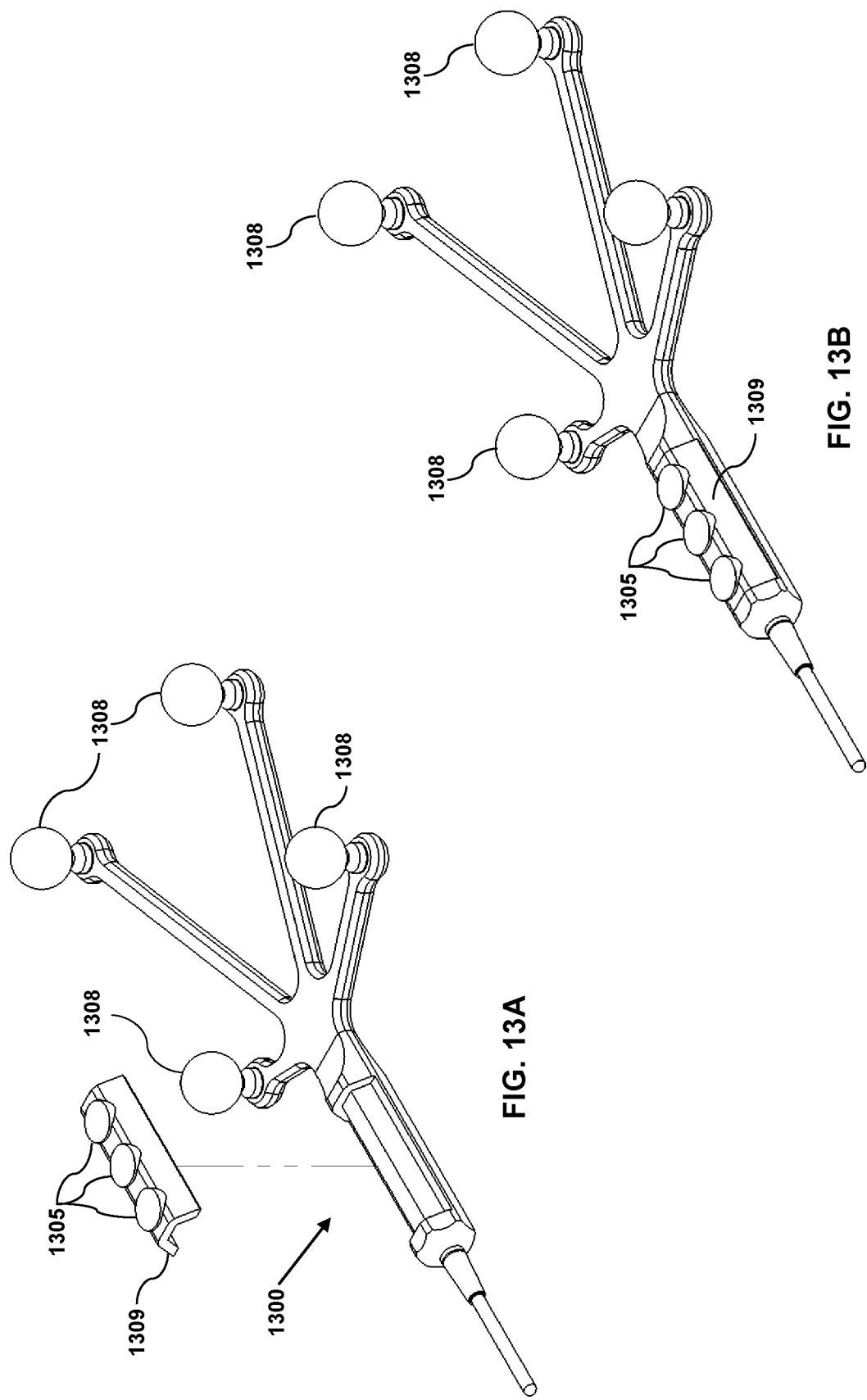

OPTICAL-BASED INPUT FOR MEDICAL DEVICES

TECHNICAL FIELD

The present application relates to input tools for medical devices and, more particularly, to optical input tools for providing input commands to medical devices.

BACKGROUND

Medical devices, such as surgical navigation systems, may be used to facilitate and enhance surgical procedures. For example, a surgical navigation system may provide imaging guidance to a surgeon operating on a patient.

Some such medical devices may require input to be provided by an operator or surgeon in order to initiate certain modes or operations on the medical device. For example, in a system which includes a robotic feature, such as a robotic arm which physically re-orients itself within a surgical environment. The robotic arm may, for example, have an image sensor provided thereon which may be used to acquire an image of a patient. In a surgical environment, the medical device may require operator input before re-orienting the robotic arm to avoid unintended consequences, such as bumping a surgeon, a surgical tool, etc.

SUMMARY

In one aspect, the present disclosure describes a system for adjusting an operating state of a medical electronic device. The system includes an optical tracking system configured to detect three or more tracking markers. The system also includes a processor coupled with the optical tracking system. The processor is programmed with instructions which, when executed, configure the processor to: configure an input command by assigning at least one operating state of the medical electronic device to a particular state of at least one of the tracking markers; await to receive a priming command from a user, the priming command being a command to prime the medical electronic device for receiving the input command; after receiving the priming command, identify a present state of the tracking markers based on data from the optical tracking system; compare the present state with the particular state assigned to the operating state; and based on the comparison, determine that an input command has been received and adjust the operating state of the medical electronic device to the assigned operating state.

In another aspect, the present disclosure describes a method performed by a processor for adjusting an operating state of a medical electronic device. The method includes: configuring an input command by assigning at least one operating state of the medical electronic device to a particular state of at least one tracking marker detectable by an optical tracking system; awaiting to receive a priming command from a user, the priming command being a command to prime the medical electronic device for receiving the input command; after receiving the priming command, identifying a present state of the tracking markers based on data from the optical tracking system; comparing the present state with the particular state assigned to the operating state; and based on the comparing, determining that an input command has been received and adjusting the operating state of the medical electronic device to the assigned operating state.

In yet a further aspect, the present disclosure describes a non-transitory processor-readable storage medium. The non-transitory processor-readable storage medium includes processor-executable instructions which, when executed, configure the processor to: configure an input command by assigning at least one operating state of the medical electronic device to a particular state of at least one tracking marker detectable by an optical tracking system; await to receive a priming command from a user, the priming command being a command to prime the medical electronic device for receiving the input command; after receiving the priming command, identify a present state of the tracking markers based on data from the optical tracking system; compare the present state with the particular state assigned to the operating state; and based on the comparing, determine that an input command has been received and adjust the operating state of the medical electronic device to the assigned operating state.

Other aspects will be understood by a person skilled in art in view of the disclosure and accompanying drawings.

BRIEF DESCRIPTION OF THE DRAWINGS

Embodiments will now be described, by way of example only, with reference to the drawings, in which:

FIG. 6 is a flow chart illustrating a method of registering a patient for a medical procedure with a medical navigation system using a patient reference device;

FIG. 12A is a perspective view of an embodiment of a pointer tool having a movable tracking marker in which the movable tracking marker is in a first position;

FIG. 12B is a perspective view of the pointer tool of FIG. 12A in which the movable tracking marker is in a second position;

FIG. 12C is a top view of the pointer tool of FIG. 12A in which the movable tracking marker is in the first position;

FIG. 12D is a side view of the pointer tool of FIG. 12A in which the movable tracking marker is in the first position;

FIG. 12E is a side view of the pointer tool of FIG. 12A taken at a tip side of the pointer tool;

FIG. 12F is a bottom view of the pointer tool of FIG. 12F in which the movable tracking marker is in the first position;

FIG. 13A is a perspective view of a tracked pointer tool in which a cartridge has been detached from the tracked pointer tool;

FIG. 13B is a perspective view of the tracked pointer tool of FIG. 13A in which the cartridge is attached;

DETAILED DESCRIPTION

Figure 1:
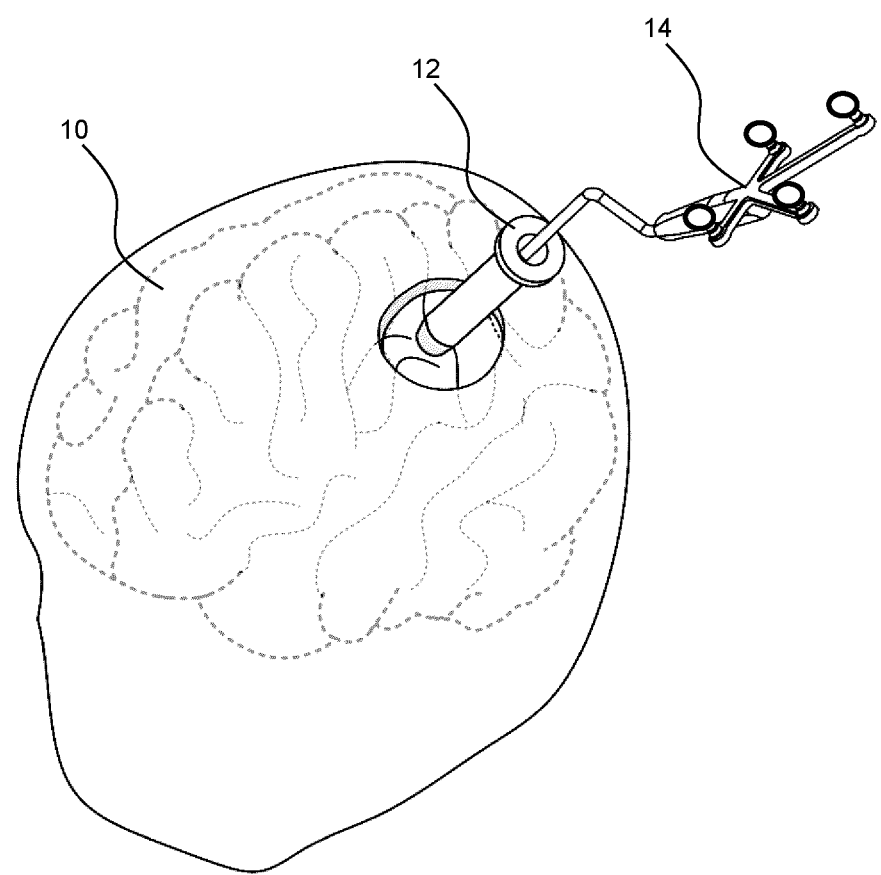
FIG. 1 illustrates the insertion of an access conduit into a human brain, for providing access to internal brain tissue during a medical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings.

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Some embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

In some embodiments, a 3D scanner, such as an optical scanner using structured light, is used to acquire a 3D scan of the patient being operated on. The 3D scan produces a 3D image of a portion of the surface of the patient, in combination with a high resolution imaging system. The "surface" of the patient is intended to mean all portions of the patient's body that would, at a given point during an operation, reflect light transmitted by a device towards the patient. For example, the surface includes any internal portions of the patient's brain that have been exposed during the operation, including any portions visible via an access port. The 3D scanner provides three dimensional images, each comprising a two dimensional array of pixels, representing the reflectance of the corresponding points on the surface of the patient, as well as depth information that may be incorporated into the images as contour lines.

The present disclosure is generally related to medical procedures, such as neurosurgery, and minimally invasive surgery to be specific.

In the example of a port-based surgery, a surgeon or robotic surgical system may perform a surgical procedure involving tumor resection in which the residual tumor remaining after is minimized, while also minimizing the trauma to the healthy white and grey matter of the brain. A beneficial input that may assist minimization of residual tumor and healthy tissue damage may be visualization of the area of interest using high resolution OCT imaging providing a greater capacity to resolve the unhealthy brain tissues.

FIG. 1 illustrates the insertion of an access port into a human brain, for providing access to internal brain tissue during a medical procedure. In FIG. 1, access port 12 is inserted into a human brain 10, providing access to internal brain tissue. Access port 12 may include instruments such as catheters, surgical probes, or cylindrical ports such as the NICO BrainPath. Surgical tools and instruments may then be inserted within the lumen of the access port in order to perform surgical, diagnostic or therapeutic procedures, such as resecting tumors as necessary. The present disclosure applies equally well to catheters, DBS needles, a biopsy procedure, and also to biopsies and/or catheters in other medical procedures performed on other parts of the body where head immobilization is needed.

In the example of a port-based surgery, a straight or linear access port 12 is typically guided down a sulci path of the brain. Surgical instruments 14 may then be inserted down the access port 12.

Optical tracking systems, which may be used in the medical procedure, track the position of a part of the instrument that is within line-of-site of the optical tracking camera. These optical tracking systems also require a reference to the patient to know where the instrument is relative to the target (e.g., a tumor) of the medical procedure. These optical tracking systems require a knowledge of the dimensions of the instrument being tracked so that, for example, the optical tracking system knows the position in space of a tip of a medical instrument relative to the tracking markers being tracked. It should be noted that any embodiments provided herein using which employ an optical tracking system may be extended to any relevant tracking system as are known in the art, and thus the examples provided below should not be taken to limit the scope of the invention as disclosed herein.

Figure 2:
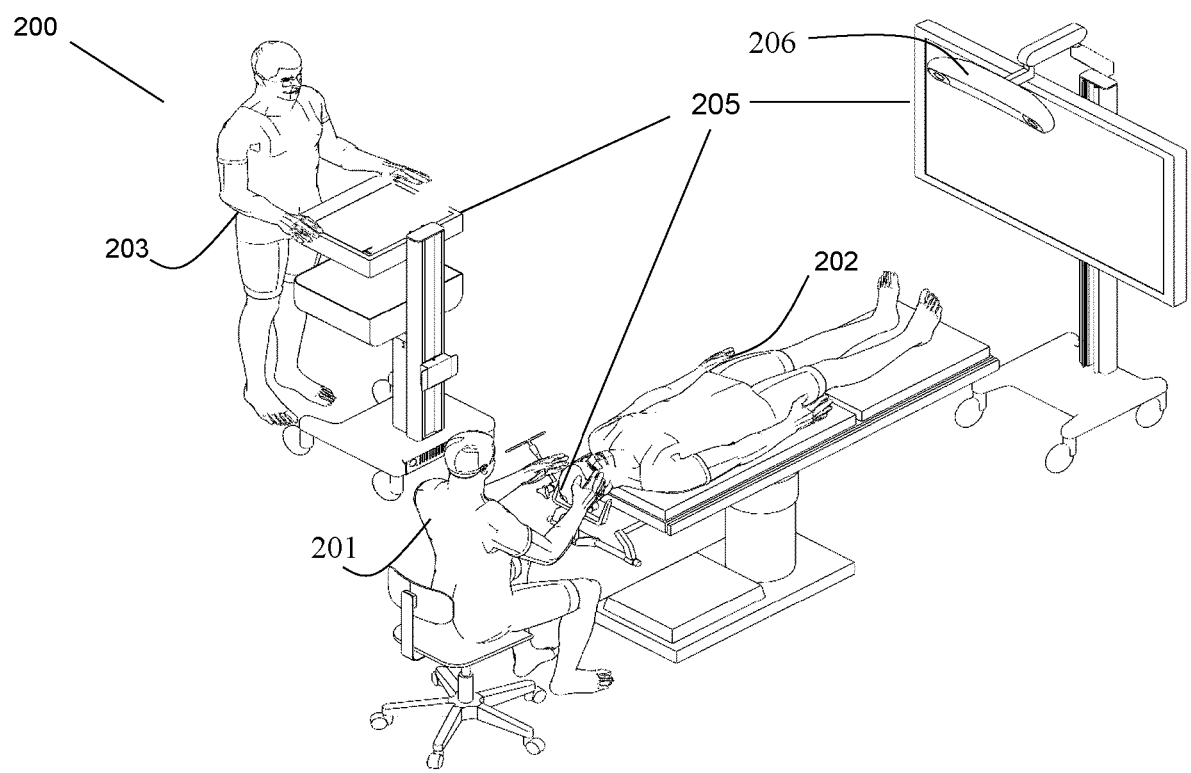
FIG. 2 shows an exemplary navigation system to support minimally invasive access port-based surgery.

Referring to FIG. 2, an exemplary navigation system environment 200 is shown, which may be used to support navigated image-guided surgery. As shown in FIG. 2, surgeon 201 conducts a surgery on a patient 202 in an operating room (OR) environment. A medical navigation system 205 comprising an equipment tower, tracking system 206 (which is an optical tracking system in the embodiment of FIG. 2), displays and tracked instruments assist the surgeon 201 during his procedure. An operator 203 is also present to operate, control and provide assistance for the medical navigation system 205. A detailed description of a surgical navigation system is outlined in international application PCT/CA2014/050270, entitled "SYSTEMS AND METHODS FOR NAVIGATION AND SIMULATION OF MINIMALLY INVASIVE THERAPY", which claims priority to U.S. Provisional Patent Application Ser. Nos. 61/800,155 and 61/924,993, which are all hereby incorporated by reference in their entirety.

Figure 3:
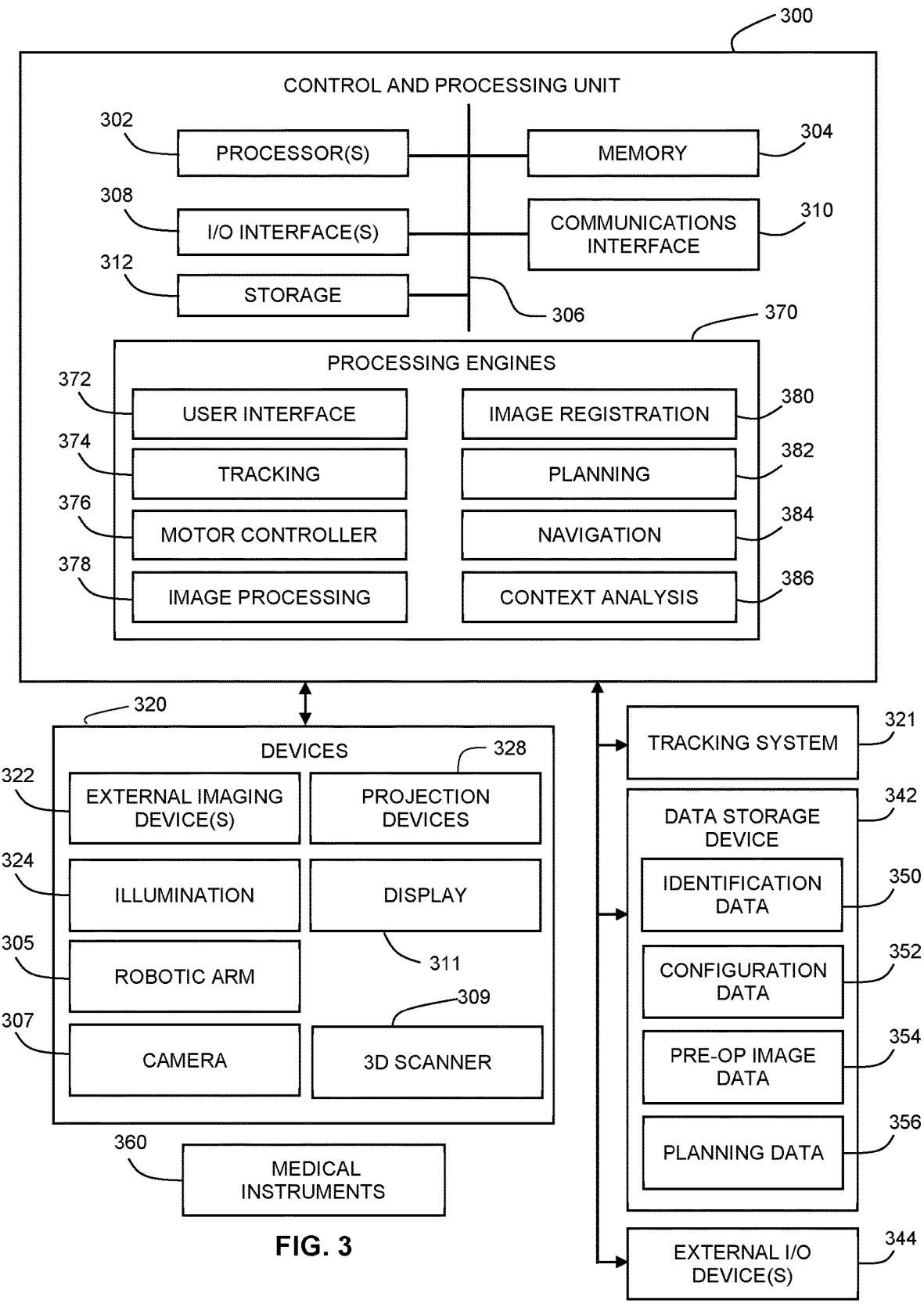
FIG. 3 is a block diagram illustrating a control and processing system that may be used in the navigation system shown in FIG. 2.

Referring to FIG. 3, a block diagram is shown illustrating a control and processing system 300 that may be used in the medical navigation system 205 shown in FIG. 2 (e.g., as part of the equipment tower). As shown in FIG. 3, in one example, control and processing system 300 may include one or more processors 302, a memory 304, a system bus 306, one or more input/output interfaces 308, a communications interface 310, and storage device 312. Control and processing system 300 may be interfaced with other external devices, such as tracking system 321, which may be the tracking system 206 of FIG. 2, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage device 342 includes identification data 350 for identifying one or more medical instruments 360 and configuration data 352 that associates customized configuration parameters with one or more medical instruments 360. Data storage device 342 may also include preoperative image data 354 and/or medical procedure planning data 356. Although data storage device 342 is shown as a single device in FIG. 3, it will be understood that in other embodiments, data storage device 342 may be provided as multiple storage devices.

Medical instruments 360 are identifiable by control and processing unit 300. Medical instruments 360 may be connected to and controlled by control and processing unit 300, or medical instruments 360 may be operated or otherwise employed independent of control and processing unit 300. The tracking system 321 may be employed to track one or more of medical instruments 360 and spatially register the one or more tracked medical instruments to an intraoperative reference frame. For example, medical instruments 360 may include tracking markers such as tracking spheres that may be recognizable by a tracking camera 307. In one example, the tracking camera 307 may be an infrared (IR) tracking camera. In another example, a sheath placed over a medical instrument 360 may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, an automated arm 305, one or more projection devices 328, one or more 3D scanning devices 309, (such as CT, MRI, structured light and etc.) and one or more displays 311. Examples of external imaging devices 322 include OCT imaging devices and ultrasound imaging devices.

Exemplary aspects of the disclosure can be implemented via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example the processing modules 370 may be stored in the memory 304 and the processing modules may be collectively referred to as processing modules 370.

It is to be understood that the system is not intended to be limited to the components shown in FIG. 3. One or more components of the control and processing system 300 may be provided as an external component or device. In one example, navigation module 384 may be provided as an external navigation system that is integrated with control and processing system 300.

Some embodiments may be implemented using processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

According to one aspect of the present application, one purpose of the navigation system 205, which may include control and processing unit 300, is to provide tools to the neurosurgeon that will lead to the most informed, least damaging neurosurgical operations. In addition to removal of brain tumors and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure.

While one example of a navigation system 205 is provided that may be used with aspects of the present application, any suitable navigation system may be used, such as a navigation system using magnetic tracking instead of infrared cameras, and or active tracking markers.

Figure 4:
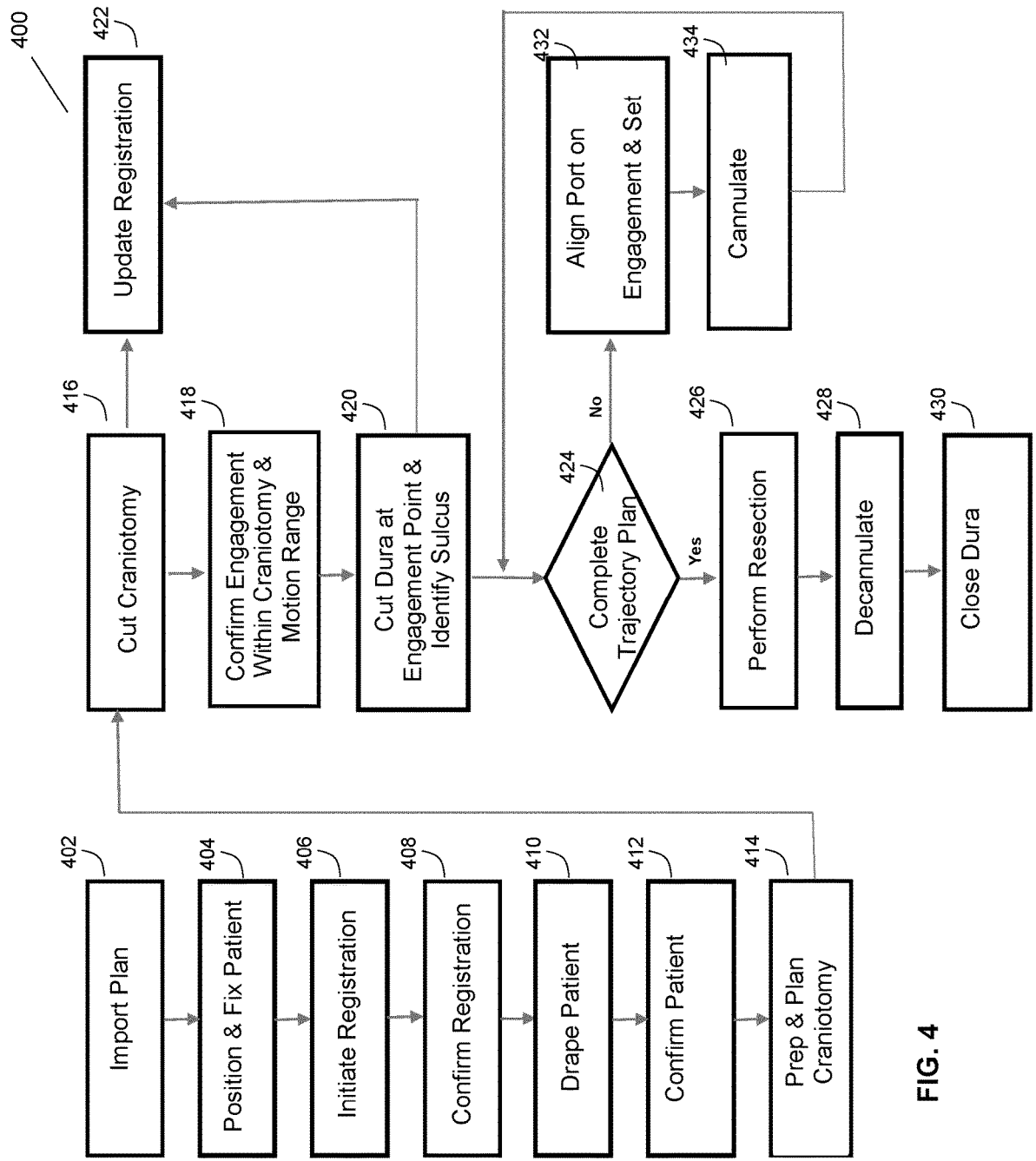
FIG. 4 is a flow chart illustrating a method involved in a surgical procedure using the navigation system of FIG. 2.

Referring to FIG. 4, a flow chart is shown illustrating a method 400 of performing a port-based surgical procedure using a navigation system, such as the medical navigation system 205 described in relation to FIG. 2. At a first block 402, the port-based surgical plan is imported. A detailed description of the process to create and select a surgical plan is outlined in international publication WO/2014/139024, entitled "PLANNING, NAVIGATION AND SIMULATION SYSTEMS AND METHODS FOR MINIMALLY INVASIVE THERAPY", which claims priority to U.S. Provisional Patent Application Ser. Nos. 61/800,155 and 61/924,993, which are all hereby incorporated by reference in their entirety.

Once the plan has been imported into the navigation system at the block 402, the patient is placed on a surgical bed. The head position is confirmed with the patient plan in the navigation system (block 404), which in one example may be implemented by the computer or controller forming part of the equipment tower 201.

Next, registration of the patient is initiated (block 406). The phrase "registration" or "image registration" refers to the process of transforming different sets of data into one coordinate system. Data may include multiple photographs, data from different sensors, times, depths, or viewpoints. The process of "registration" is used in the present application for medical imaging in which images from different imaging modalities are co-registered. "Registration" is also used in the present application to map a preoperative image of a patient to that patient in a physical tracking space.

Those skilled in the relevant arts will appreciate that there are numerous image registration techniques available and one or more of the techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include image registration of brain computerized tomography (CT)/MRI images or PET/CT images for tumor localization, registration of contrast-enhanced CT images against non-contrast-enhanced CT images, and registration of ultrasound and CT to patient in physical space.

Figure 5:
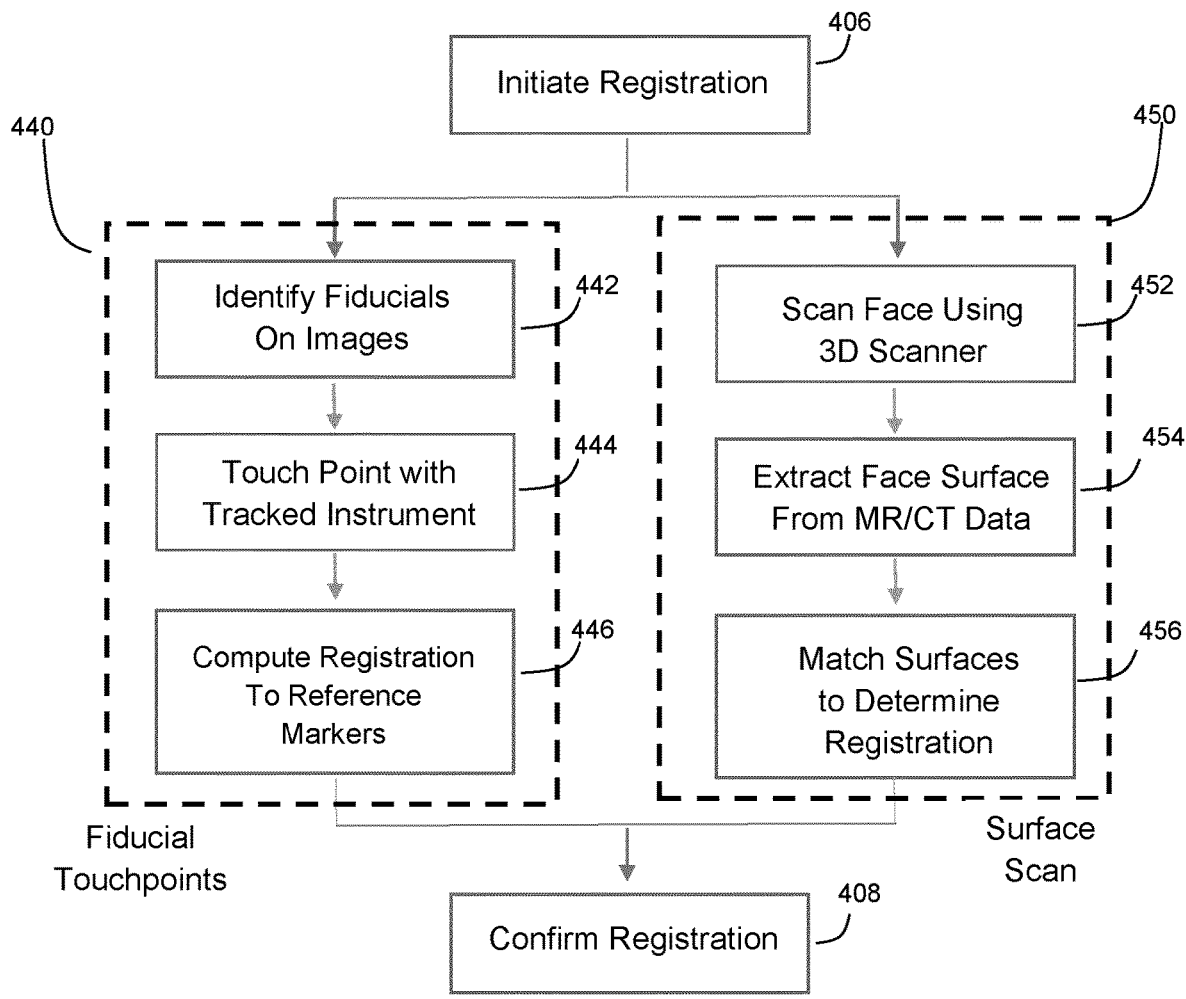
FIG. 5 is a flow chart illustrating a method of registering a patient for a surgical procedure as outlined in FIG. 4.

Referring now to FIG. 5, a flow chart is shown illustrating a method involved in registration block 406 as outlined in FIG. 4 in greater detail. If the use of fiducial touch points (440) is contemplated, the method involves first identifying fiducials on images (block 442), then touching the touch points with a tracked instrument (block 444). Next, the navigation system computes the registration to reference markers (block 446).

Alternately, registration can also be completed by conducting a surface scan procedure (block 450). The block 450 is presented to show an alternative approach, but may not typically be used when using a fiducial pointer. First, the face is scanned using a 3D scanner (block 452). Next, the face surface is extracted from MR/CT data (block 454). Finally, surfaces are matched to determine registration data points (block 456).

Upon completion of either the fiducial touch points (440) or surface scan (450) procedures, the data extracted is computed and used to confirm registration at block 408, shown in FIG. 4.

Referring back to FIG. 4, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms (e.g., bacteria) between non-sterile and sterile areas. At this point, conventional navigation systems require that the non-sterile patient reference is replaced with a sterile patient reference of identical geometry location and orientation. Numerous mechanical methods may be used to minimize the displacement of the new sterile patient reference relative to the non-sterile one that was used for registration but it is inevitable that some error will exist. This error directly translates into registration error between the surgical field and pre-surgical images. In fact, the further away points of interest are from the patient reference, the worse the error will be.

Upon completion of draping (block 410), the patient engagement points are confirmed (block 412) and then the craniotomy is prepared and planned (block 414).

Upon completion of the preparation and planning of the craniotomy (block 414), the craniotomy is cut and a bone flap is temporarily removed from the skull to access the brain (block 416). In some procedures registration data is updated with the navigation system at this point (block 422).

Next, the engagement within craniotomy and the motion range are confirmed (block 418). Next, the procedure advances to cutting the dura at the engagement points and identifying the sulcus (block 420).

Thereafter, the cannulation process is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Once cannulation is complete, the surgeon then performs a resection or the like (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of FIG. 4 are specific to port-based surgery, such as portions of blocks 428, 420, and 434, but the appropriate portions of these blocks may be skipped or suitably modified when performing non-port based surgery.

Referring now to FIG. 6, a registration process, similar to that which may be used in block 450 of FIG. 5, is shown for computing a transform that may be used to import coordinates from the physical coordinate space of the operating room to the image space of the MRI image, CT image, or image of another type. Resultantly any tool positions in the physical coordinate space may be registered to the image space via the application of this transform.

In order to derive this transform for importing objects from a physical coordinate space to an image space, the two spaces must be coupled with a "common reference", having a defined position that can be located in both the physical and image coordinate spaces. The process of patient registration for surgical navigation uses identifiable points located on a patient anatomy visible both on the patient and on the patients scan as the common reference point(s). An example of a common reference is shown in FIG. 6 as 601 along with the physical and image coordinate space origins, 611 and 621 respectively. It is apparent from the figure that the common references position is known in both spaces. Using these positions a transform may be derived that facilitates the importation of the position of any point in the physical coordinate space into the image space. One way to determine the transform is by equating the locations of the common reference in both spaces and solving for an unknown translation variable for each degree of freedom defined in the two coordinate spaces. These translation variables may then be used to convert a set of coordinates from one space to the other. An exemplary transform may be derived as per the diagram shown in FIG. 6. In the figure the position of the common reference 601 is known relative to the physical coordinate space origin 611 and the image space origin 621. The common references position may be extracted from the diagram as follows:

$$(Xcra, Ycra) = (55,55)$$

and $$(Xcrv, Ycw) = (-45,-25)$$

Where the subscript "cra" denotes the common reference position relative to the physical coordinate space origin and the subscript "cry" denotes the common reference position relative to the image space origin. Utilizing a generic translation equation describing any points ((Ya, Xa) and (Yv, Xv)), where the subscript "a" denotes the coordinates of a point relative to the physical coordinate space origin 611, and the subscript "v" denotes the coordinates of a point relative to the image space origin 621, we can equate the individual coordinate elements from each space to solve for translation variables ((YT, XT)), where the subscript "T" denotes the translation variable as shown below.

$$Yv = Ya + YT$$

$$Xv = Xa + XT$$

Now substituting the derived values of the points from FIG. 6 we can solve for the translation variable.

$$-45 = 55 + YT$$

$$YT$$

And $$-25 = 55 + XT$$

$$80 = XT$$

Utilizing these translation variables, any position (i.e. (Ya, Xa)) defined relative to the common reference in the physical coordinate space may be transformed into an equivalent position defined relative to the common reference in the image space through the two generic transformation equations provided below. It should be noted that these equations may be rearranged to transform any coordinates of a position from the image space into equivalent coordinates of a position in the physical coordinate space as well.

$$Xa = Xv + 100$$

and $$Ya = Yv + 80$$

The resulting transform thus enables the position of any object to be transformed from the physical coordinate space to the image space. Thus the two spaces become coupled with the transform enabling the registration of objects from the physical space to the image space. It should be noted that in practice the common reference is usually a set of points (as opposed to a single point) from the patients anatomy that may be located both on the anatomy of the patient in the physical coordinate space of the operating room and in the image of the patient. Using a set of points may be more advantages than a single point as it further restricts degrees of freedom and thus more accurately defines an objects position in space. More specifically in a spatial coordinate system such as the physical coordinate space of the operating room an object may have six degrees of freedom, three spatial degrees of freedom most commonly referred to as (x, y, z) and three rotational degrees most commonly referred to as (pitch, yaw, roll) that may be used to define the object position entirely. Accordingly one manner to transfer these degrees of freedom upon transformation from the physical coordinate space to the image space is to apply the transform to three or more points on the object.

Figure 7:
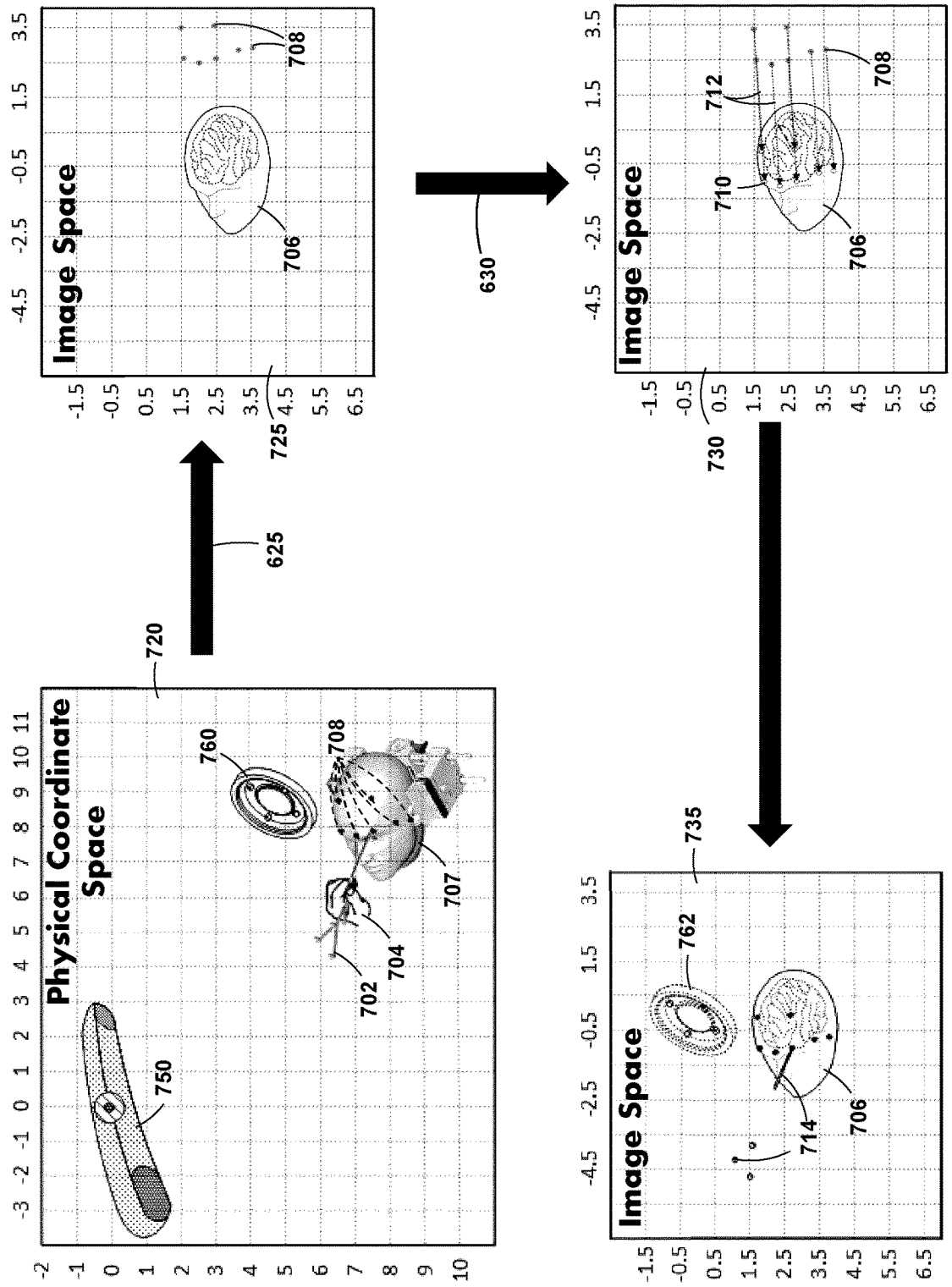
FIG. 7 is diagram illustrating the process of patient registration.

To further elaborate on the process of registration a practical implementation will be described in further detail as follows. A flow chart describing the practical method of performing a patient registration is provided in FIG. 6. The registration method 602 describes a touch-point registration method. FIG. 7 shows an illustrative diagram of each step in performing a registration using the touch-point method 602. In an embodiment these methods may be executed via the use of a navigation system such as shown in FIG. 3 and any steps may be programmed into the navigation system processor 300, stored in memory 304, and called upon by the navigation system as required.

The first step in this method 600 is to initialize the touch-point acquisition process. During this step a user may prompt the navigation system processor such as processor 302 in FIG. 3 to initiate said touch-point acquisition process. To clarify, a touchpoint acquisition process may refer to the priming of the system to acquire a pointer position upon determining the pointer to be at the position of a fiducial point. In an alternate embodiment the system itself may initiate a touch-point registration process without the input of the user, such as upon the system workflow advancing to the touch-point registration mode, or upon the detection of specific trackable medical instruments such as by tracking system 321.

Once the touch-point registration process is initiated 600 the following step is to acquire one or more fiducial positions 605 in the physical coordinate space of the operating room. FIG. 7 depicts an illustration of this step as 625. As is shown in the figure a user 704 is identifying fiducials 708 on a patient 706 using a tracked pointer tool 702. The tracking camera 750, connected to the surgical navigation system, collects the positions of the fiducial points 708 via the tracked pointer tool 702 and passes them to the navigation system processor which either stores the points in the image space containing the patient image, such as the points 708 in the image space 725, or alternatively in memory. In some cases the tracking system is constantly tracking the pointer tools position thus in order to record the position of the pointer tool at the correct time (i.e. when it is placed on a fiducial), the system may be prompted by the user. This prompt may be facilitated through the use of a switch type device such as a foot pedal or mouse that are connected to the surgical navigation system, or through the use of input techniques described below with reference to FIGS. 9 to 13E.

Once the fiducial points are acquired 605 the following step is to extract the scanned fiducial points from the patient image 610. FIG. 7 depicts an illustration of this step 630. As is shown in the figure the scanned fiducials 710 are segregated from the rest of the patient image 706 in the image space 730. In some cases the segregation of the fiducials from the image of the patient may be completed manually by a user. Where the user indicates the fiducial positions on the patient image to the surgical navigation system through a graphical user interface. While in other cases the surgical navigation system may be programmed with instructions to segregate the positions of the scanned fiducials from the patient image automatically. Thus step 610 may be performed by either a user or a surgical navigation system.

Figure 8:
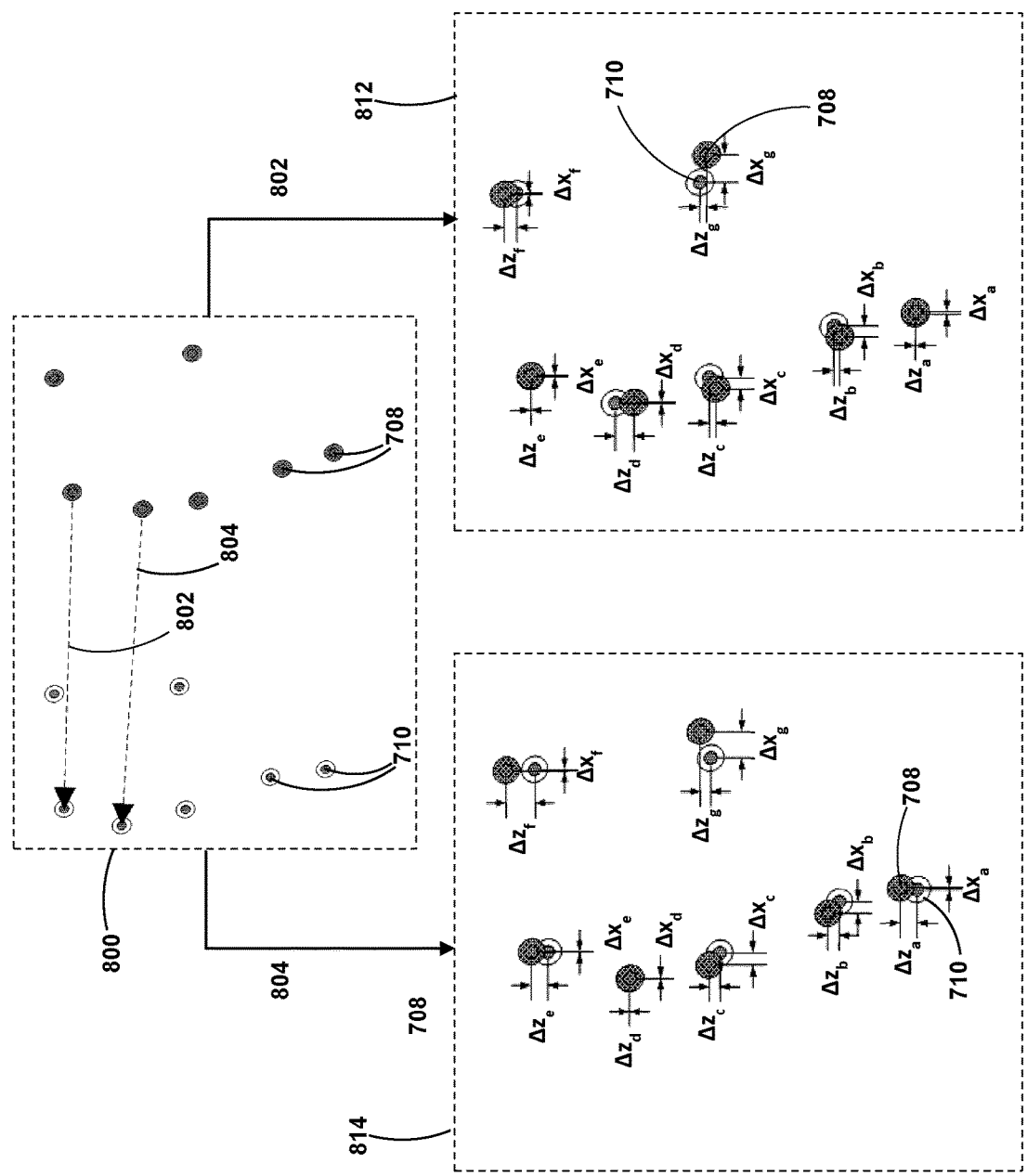
FIG. 8 is a diagram illustrating the process of deriving a patient registration transform.

Once the scanned fiducial points are extracted from the patient image 610 the following step is to compute a best fit transform 615. FIG. 7 depicts an illustration of a computed transform 712 as per the example provided. It is apparent from the figure that the transform 712 is computed such that the fiducial points 708 acquired from the physical coordinate space align with the extracted fiducials 710. In general the completion of this step 615 requires the navigation system processor to compute a single transform that when applied to each fiducial point 708 in the image space individually, will align them with their scanned fiducial counterparts 710. However given practical limitations of technology perfect alignment is problematic to achieve for all of the fiducial points using a single transform. Thus to approximate a perfect alignment the processor instead derives a transform that minimizes the deviation in alignment between the extracted fiducials from the patient image and the fiducial points on the patient. For example as shown in FIG. 8 the transforms 802 and 804 both attempt to align the fiducial points 708 with their counterparts 710 in the image space 800. Such transforms may be derived by iteratively applying a cost minimization function to the initial set of fiducial points with arguments being the sum of spatial deviances $\Delta x_{a \to g}$ and $\Delta z_{a \to g}$ between the two sets of points 708 and 710. In one example, the iterative cost minimization function may take the form of an Iterative Closest Point (ICP) approach to calculate the registration transformation, such as that detailed in "A Method for Registration of 3-D Shapes" by Paul J. Besl and Neil D. McKay, IEEE Transactions on Pattern Analysis and Machine Intelligence, pp. 239-256, VOL. 14, No. 2, February 1992, the entirety of which is hereby incorporated by reference. However, any suitable approach may be used depending on the design criteria of a particular application. For example as shown in FIG. 8 the iterative computation may in one iteration produce the transform 804 that when applied to the fiducial points 708 produces the alignment of points shown in frame 814 of FIG. 8. While in a subsequent iteration may produce the transform 802 that when applied to the fiducial points 708 produces the alignment of points shown in frame 812 of FIG. 8. The processor may then execute the cost minimization function to compare the sum of the deviances $\Delta x_{a \to g}$ and $\Delta z_{a \to g}$ for each result 814 and 812 and select the one with the lowest value for the next iteration and so on until the deviation value falls below a certain threshold value or meets some alternately defined criteria. It is apparent from the case shown in FIG. 8 that the transform which minimizes the spatial deviances $\Delta x_{a \to g}$ and $\Delta z_{a \to g}$ when applied to the fiducial points 708 is the transform 812.

Referring back to FIG. 6, once step 615 is completed and a transform is derived it may then be used to transform any points from the physical coordinate space of the operating room into the image space, effectively coupling the two spaces. Referring back to FIG. 7 this aspect of the patient registration process is illustrated by the physical coordinate space 720 and the image space 735 where the spatial alignments between the patient 707, the patient reference 760, and the pointer tool 702 is duplicated by the virtual representations of these objects in the image space 720. i.e. by the patient scan 706, the virtual patient reference 762 and the virtual pointer tool 714 in the image space 735.

In at least some embodiments, a tracked pointer tool 702 (FIG. 7) or another tracked medical instrument may, in addition to the functions described above, be used for inputting an input command to a medical electronic device such as a medical navigation system 205 of the type described above with reference to FIG. 2, or another medical device.

Such input commands may be used to adjust an operating state of the medical electronic device. By way of example, the input command may control an automatic arm which may be used to assist with imaging, input a selection, variable or parameter, or cause another action associated with the medical electronic device to be performed.

That is, an operator (such as the operator 203 of FIG. 2 or the surgeon 201 of FIG. 2) may interact with a tracked medical instrument (such as the tracked pointer tool) in a particular manner in order to cause the medical electronic device to determine that an input command has been received. For example, in some embodiments, the medical electronic device may receive the input command when it determines that the tracked medical instrument is in a location associated with a virtual interface element, such as a virtual button, a virtual dial, a virtual trackpad, a virtual scroll bar, etc. In at least some embodiments, the location of the virtual interface element, may be assigned during a calibration routine. For example, the medical electronic device may be configured to prompt a user to place the tracked medical instrument in a location that is to be assigned to a virtual button. In other embodiments, the medical electronic device may identify the location of the virtual interface element by identifying fixed tracking markers which are located at predetermined locations relative to the virtual interface element. For example, in some embodiments, a fixture may be provided which includes three or more tracking markers and a virtual element may be located at a predetermined distance from the tracking markers.

The following description refers to tracked pointer tools and, in some instances, this may be referred to as a pointer tool, a pointer, or a tracked pointer.

An overview having been provided, reference will now be made to FIG. 9, in which a flowchart of an example method 900 is illustrated. The method 900 may be performed by a system for adjusting an operating state of a medical device, such as a medical electronic device. For example, the method 900 may be performed by a medical electronic device, which may be a medical electronic device of a type described herein; for example, a medical navigation system 205 as described above with reference to FIG. 2. In some embodiments, the method 900 may be implemented by a control and processing system 300 of the type described above with reference to FIG. 3. In some embodiments, the method 900 may be implemented by a controller, such as a processor 302 (FIG. 3) which is programmed with instructions which, when executed, configure the controller to perform the method 900 of FIG. 9.

The controller is coupled with a tracking system 206 (FIG. 2), 321 (FIG. 3), such as an optical tracking system, that is configured to detect one or more tracking markers. In at least some embodiments, the optical tracking system is configured to detect three or more tracking markers. The tracking markers may, for example, be tracking spheres that are recognizable by a tracking camera 307 (FIG. 3) associated with the medical electronic device. As will be described below, in at least some embodiments, at least some of the tracking markers may be provided on a pointer tool 702 (FIG. 7) or another tracked medical instrument. Thus, the pointer tool 702 may, in some embodiments, provide multiple functions—it may be used to identify fiducials in the manner described above with reference to FIGS. 6 and 7, and it may be used to also provide an input command to the medical electronic device as described below.

The description of the method 900 that follows generally refers to operations that are performed by the medical electronic device. It will be understood that these operations may be performed by a processor associated with the medical electronic device.

At operation 902, the medical electronic device configures an input command by assigning at least one operating state of the medical electronic device to a particular state of at least one of the tracking markers. The operating state may, for example, be a particular mode, function, or operation on the medical electronic device and the input command may, for example, be a selection command, a command to modify or set a parameter value, etc.

By way of example, in one embodiment, the medical electronic device may include an automatic arm, which may also be referred to as a robotic arm 305 (FIG. 3). A camera may be mounted on the robotic arm, for example, to provide imaging. In at least some embodiments, the input command configured at 902 may be one that relates to the use of the robotic arm. For example, in one embodiment, the input command may instruct the medical electronic device to reorient the robotic arm. That is, the operating state of the medical electronic device that is assigned at operation 902 may involve movement of the robotic arm.

At operation 902, the input command is configured by assigning a specific operating state of the medical electronic device to a particular state of at least one of the tracking markers. The particular state of the tracking marker(s) is a physical state of the tracking marker(s), such as a specific physical location in space or a "covered" state, which is found to exist when the tracking marker(s) is covered (e.g., by an operator's hand or finger) and, therefore, not visible to the optical tracking system.

After the input command is configured, at operation 904 the medical electronic device identifies the present state of the tracking marker(s) based on data from the optical tracking system. That is, the medical electronic device tracks the tracking markers. For example, the medical electronic device may determine the location, in space, of the tracking markers. In some embodiments, the medical electronic device may determine whether one or more of the tracking markers are in the "covered" state, in which such tracking markers are not visible to the optical tracking system. The tracking markers may be provided on a tracking instrument or tracked mechanism such as, for example, a fixture, tracking tree, pointing tool, or frame. Example tracking instruments are described below.

At operation 906, the medical electronic device compares the present state of the tracking marker(s) with the particular state that was assigned to the operating state at operation 902. For example, in an embodiment in which the particular state that was assigned at operation 902 is a specific location in space, at operation 906, the medical electronic device determines whether the tracking marker(s) are in that location.

By way of further example, in an embodiment in which the particular state that was assigned at operation 902 is a "covered" state in which at least one of the tracking markers is covered (e.g., by an operator's hand or finger) and not visible to the medical electronic device, then at operation 906, the medical electronic device determines whether that tracking marker is covered.

At operation 908, the medical electronic device determines, based on the comparison, whether an input command has been received. An input command is determined to have been received when the present state of the tracking marker(s) indicates the particular state that was assigned to the operating state at operation 902. That is, the input command is determined to have been received when the tracking marker(s) have a physical state that is associated with the input command. For example, in some embodiments, the input command is determined to have been received at operation 908 when, based on the comparison at operation 906, it is determined that the tracking markers indicate a physical location, in space, associated with the input command (i.e., a physical location assigned to the operating state at operation 902). The physical location in space that is associated with the input command may be a physical point which may be defined, for example, relative to another point in space, which may be a point that is statically positioned or dynamically positioned (e.g., it this reference point may dynamically move in the space).

By way of further example, in some embodiments, the input command is determined to have been received at operation 908 when the medical electronic device determines, based on the comparison, that a particular one of the tracking markers is covered (i.e., is in a covered state). For example, when an operator has covered one of the tracking markers, the medical electronic device may determine that an input command has been received. In an alternate example, the uncovering of a tracking marker that is normally covered may also induce such a command, if the system is configured to do so.

To prevent erroneous detections of input commands, the "covered" state may only be determined, by the medical electronic device, to exist when a further one or more of the tracking markers are visible to the medical electronic device. For example, a plurality of tracking markers which face a common direction may be provided on a common medical instrument. In this orientation, when one of the tracking markers is visible to the medical electronic device, all of the tracking markers should be visible to the medical electronic device. Thus, when one of the tracking markers is visible but another of the tracking markers is not visible, the medical electronic device may conclude that the invisible tracking marker is in a covered state. However, when all of the tracking markers are not visible, the medical electronic device may determine that the tracking markers are not visible since the medical instrument is not located within a sensing area associated with the optical tracking system or since the medical instrument is oriented in an incorrect direction (e.g., a direction where the tracking markers do not face a camera associated with the optical tracking system).

The input command may also be determined to have been received in some embodiments when the medical electronic device determines, based on the comparison, that a particular one of the tracking markers is uncovered (i.e., is in an uncovered state). For example, when an operator has uncovered one of the tracking markers that was previously covered, the medical electronic device may determine that an input command has been received.

If an input command has not been received, then the medical electronic device may, at operation 904, continue to identify a present state of the tracking markers to detect if an input command is received sometime thereafter.

If, however, an input command is determined to have been received, then at operation 910 the medical electronic device adjusts the operating state of the medical electronic device to an assigned operating device. For example, in some embodiments, the medical electronic device may adjust its operating state to cause a robotic arm to be activated. In other examples the user interface of the electronic medical device may be altered, such as upon a selection of a menu item.

In some embodiments, an example of which will be described more fully below with reference to FIGS. 13A to 13E the medical electronic device is configured to have a two stage trigger before performing certain operations (e.g., repositioning a robotic arm). The two stage trigger requires an operator to issue two different input commands before the operation is performed. For example, in one embodiment, the first action may involve covering a first one of the tracking markers and the second action may involve covering a second one of the tracking markers while the first one of the tracking markers remains covered. In some such embodiments, at operation 910, when the first action has been detected, the operating state may be adjusted to a "primed" operating state in which the medical electronic device monitors for a second stage of a trigger. The current operating state may be defined in memory associated with the medical electronic device and adjusting may include updating memory to reflect the primed operating state. When in the primed operating state, the method 900 may resume at operation 904, and, at operations 906 and 908, the medical electronic device determines whether the second action has been performed in order to determine whether the input command associated with the second stage of the trigger has been received. If the second stage of the trigger is received when the medical electronic device is in the primed state, then the operation associated with the two stage trigger may be performed. If, however, another condition is met prior to the second stage of the trigger being received (e.g., a timeout condition expires, another input command is received, etc.), then the medical electronic device may transition out of the primed state and into a regular operating mode. In this regular operating mode, the operation that is associated with the two stage trigger is only performed if the two stage trigger is input, beginning with the first stage of the trigger.

Figure 9:
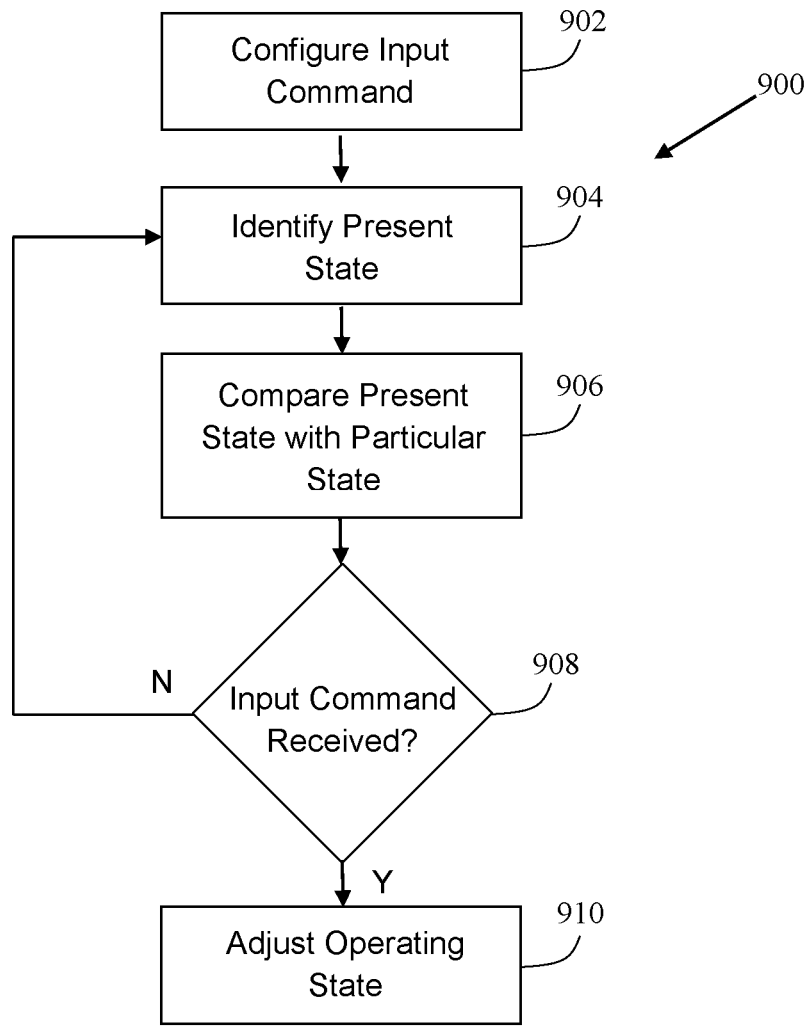
FIG. 9 is a flow chart illustrating a method of adjusting an operating mode on a medical electronic device based on optical input.

Accordingly, the method 900 of FIG. 9 may allow an input command to be input to a medical electronic device by interacting with tracking markers that are trackable by the medical electronic device.

The manner by which an operator must interact with the tracking markers in order to issue the input command may be specified during a calibration mode. For example, in some embodiments, the medical electronic device enters a calibration mode in which an operator is permitted to define a physical state of the tracking marker(s) that will be associated with the input command.

By way of example, in some embodiments, the medical electronic device may, during operation 902, define a location of a virtual interface element. This virtual interface element may, for example, be a virtual button, a virtual dial, a virtual trackpad, a virtual slider, a virtual scroll bar, etc. The location may be defined during a calibration mode.

By way of example, in one embodiment, a location of a virtual button is defined during operation 902. The virtual button is a location in space of the virtual button. During the calibration mode, an operator may move the tracking marker(s) to a location which identifies the virtual button. By way of example, in some embodiments, the location of the virtual button may be defined at operation 902 when an operator places a tip or end of a pointer tool on which the tracking markers are provided at a location in space where the virtual button is to reside. For example, one example, the tracking markers may be provided on a pointer tool which has a tip or end that may be used as a pointing surface. The tip or end is located at a predetermined distance from the tracking markers so that the medical electronic device determines the location in space of the tip or end based on the location of the tracking markers on the pointer tool. An example of a pointer tool having such a tip is illustrated in FIG. 10.

The location at which the virtual button (or other interface element) is located may be recorded in memory of the medical electronic device at operation 902.

The operator may also mark the location of the virtual button with a visual indicator, such as tape or ink, to allow the location of the button to be easily identified when the operator wishes to later enter the input command. In this way, both the medical electronic device and the operator have effectively recorded the location of the virtual button so that the location may be identified in the future.

Then, sometime later when an operator wishes to activate the virtual button, the operator again moves the pointer tool so that the tip or end of the pointer tool is located at this same location.

In an embodiment in which a virtual button is used to issue an input command to the medical electronic device, comparing (at 906) may include comparing the location of the tracking markers to determine whether the present state (i.e., the present location) of the tracking markers indicates activation of the virtual button.

If, at operation 906, the medical electronic device determines that the tip of the pointer tool is in this location (i.e., the location assigned to the virtual button), then at operation 908, a determination is made that an input command has been received and, at operation 910, the operating state of the medical electronic device is adjusted.

In some embodiments, to reduce erroneous activations of the virtual button, certain conditions must be satisfied before the virtual button (or other interface element) is determined to be activated and before an input command has been determined to have been received. For example, in one embodiment, a virtual button will only be determined to have been activated and the input command received if the medical electronic device determines that the tip or end of the pointer tool has been placed at the location in space where the virtual button is located for at least a predetermined period of time. This period of time may be referred to as a dwell time. For example, if the pointer tool is placed in the assigned location (i.e., if the tip or end is brought into this location) for at least the minimum period of time, then the input command may be determined to have been received (at operation 908). However, if the pointer tool is placed in the assigned location for a time that is less than the minimum period of time and then moved away, then the input command may be determined not to have been received (at operation 908). Thus, determining that an input command has been received may include determining that a virtual button (or other interface element) has been activated for at least a minimum dwell time.

In some embodiments, the virtual button may be activated with a "single tap." That is, when the medical electronic device determines that the pointer tool has been brought into the assigned location, then the virtual button may be considered to have been activated. However, in other embodiments, the button may be activated by performing a predetermined gesture on the virtual button. For example, in some embodiments, the virtual button may be activated with a double-tap gesture which is characterized by contacting the virtual button, moving the pointer away from contacting the virtual button, and then contacting the virtual button again within a maximum period of time. Similarly, in some embodiments, the virtual button may be activated with a triple-tap gesture. Accordingly, in at least some embodiments, at operation 908, in determining whether an input command has been received, the medical electronic device may determine whether the virtual button (or other interface element) has been activated with the predetermined gesture. In at least some embodiments, multiple virtual buttons may be engaged in order to input more complicated commands. For example, in some embodiments, multiple virtual buttons may be activated in a predetermined pattern in order to issue an input command to the medical electronic device. In such embodiments, the medical electronic device may determine that an input command has been received when virtual buttons have been engaged in a predetermined pattern of engagement. Such as covering a first marker followed by covering a second marker while uncovering the first marker, and finally covering a third and first marker while uncovering the second marker, or any combination thereof that allows the system to determine that a certain sequence has been implemented to induce an action.

In yet another example, the medical electronic device may determine that an input command has been received when a pointer tool is spun or rotated. Upon observing such spinning or rotation, followed by a period in which the spinning or rotation ceases (i.e., followed by a "dwell"), the medical electronic device may determine that an input command has been received.

The medical electronic device may also be configured with a volumetric threshold which may be used, at operation 908, to determine whether an input command has been received. For example, in some embodiments, the input command may be determined to have been received when the tip of the pointer is placed "near" the physical location of the virtual button (or other interface element). The tip of the pointer may be considered to be placed "near" the physical location when it is within a zone around the button's physical location that is defined by the volumetric threshold. By way of example, in an embodiment, the volumetric threshold is two cubic centimeters; however, other thresholds may be used in other embodiments.

The virtual interface element may take other forms, apart from a virtual button. For example, in one embodiment, the virtual interface element is a virtual dial. In some such embodiments, at operation 902, the input command is configured by defining a path associated with a virtual dial. More specifically, the medical electronic device, during a calibration mode, tracks the tracking markers of the pointer tool to record a path that will be associated with the virtual dial. More specifically, an operator moves the pointer tool so that the tip of the pointer tool follows a path that will be associated with the virtual dial. The medical electronic device records this path (e.g., by recording information about the physical location in space that defines this path). In other embodiments, the calibration step may involve the selection of predefined spatial dials that an operator may place. For example, in some embodiments an operator may place a virtual rectangular switch having three selection states and being of a predetermined size and orientation. The operator may place such a switch by indicating three points defining a plane on which the virtual switch will be placed and another point to indicate the center of the switch and rotation.

An operator may mark the path with ink or tape so that the operator is later able to locate the path. For example, in some embodiments, the path may be located on the top of a table and the operator may mark the top of the table to indicate the location of the path.

After the virtual dial has been defined, the operator may interact with the virtual dial to issue input commands to the medical electronic device. For example, the medical electronic device may, at operation 906, compare the present location of the tracking markers with the path of the virtual dial to determine whether the virtual dial has been activated (at operation 908). In some embodiments, at operation 908, the medical electronic device determines whether the virtual dial is activated in a first direction (e.g., a clock-wise direction) or whether the virtual dial is activation in a second direction (e.g., a counter-clock-wise direction). Activation in the first direction occurs when the pointer tool is moved along the path of the virtual dial in a first direction and activation in the second direction occurs when the pointer tool is moved along the path of the virtual dial in a second direction. Activation in the first direction may be associated with a different input command than activation in a second direction. For example, activation in a first direction may be associated with an input command to increase a parameter (e.g., volume), while activation in the second direction may be associated with an input command to decrease that parameter. Thus, the adjustment that is made at operation 910 may depend on a direction associated with the activation.

In at least some embodiments, the medical electronic device allows a virtual scroll bar or virtual slider to be defined by defining two terminal points associated with the virtual scroll bar (i.e., end points). The two terminal points are defined such that a path between the terminal points is defined. The path is a straight line between the two terminal points. The terminal points may be defined during a calibration mode. For example, in some embodiments, during operation 902 of the method 900, the medical electronic device prompts an operator to define the terminal points and/or the path of the virtual slider or virtual scroll bar. The operator defines the terminal points by moving the tracked pointer to the terminal points (e.g., so that the tip of the pointer touches the terminal points) and may define the path by moving the tracked pointer along the path between the terminal points (or the path may defined by the medical electronic device by inferring the path from the terminal points). The medical electronic device may observe the movement of the tracked pointer and record the terminal points and/or the path. In some embodiments, the medical electronic device, at operation 902, assigns the locations defined by the terminal points to certain functions of the medical electronic device. For example, a first one of the terminal points may be assigned with a lower end of a range of parameters and a second one of the terminal points may be assigned with a higher end of the range of parameters. A continuum of parameters between the lower end of the range and the higher end of the range may be assigned to locations between the terminal points.

After having defined the terminal points and/or the path associated with the input command, at operation 906, the medical electronic device compares the present location of the pointer tool with the locations of the terminal points and/or path. If the location of the tracking markers suggests that the terminal points and/or path have been activated by the pointer tool, then an input command may be determined to have been received (at operation 908). The input command that is determined to have been received may be one that is associated with the parameter value assigned to the terminal point which has been activated. For example, if the tip of the tracked pointer contacts the first one of the terminal points, then an input command associated with the lower end of the range of parameters is determined to have been received. Similarly, if the tip of the tracked pointer contacts the second one of the terminal points, then an input command associated with the upper end of the range is determined to have been received.

In some embodiments, at operation 908, a direction of movement along the path may also be considered. For example, the operator may move the pointer tool along the path in a first direction to input a first command (e.g., a scroll in a first direction) and may move the pointer tool along the path in a second direction to input a second command (e.g., a scroll in a second direction). Thus, in some embodiments, at operation 908, the medical electronic device determines whether the tracking markers suggest movement along the path in the first direction and whether the tracking markers suggest movement along the path in the second direction. When the movement is in the first direction, at operation 910, the medical electronic device adjusts its operating state in a manner that is different than when the movement is in the second direction. For example, when the movement is in the first direction, a displayed page may be scrolled in a first direction and when the movement is in the second direction, the display page may be scrolled in the second direction, which is generally opposite the first direction.

In some embodiments, the virtual interface element that is configured and activated in the method 900 may be a trackpad or virtual mouse. For example, in at least some embodiments, a trackpad area may be defined at operation 902 during a calibration mode of the medical electronic device. The trackpad area may be defined when an operator moves the pointer tool in a manner that allows the tracking area to be detected by the medical electronic device. For example, the pointer tool may be moved such that a tip or end of the pointer tool is moved along the perimeter of the trackpad area, or the pointer tool may be placed at a three or more locations which define the vertices of a polygon trackpad area. The medical electronic device, observes such movement during the calibration mode and records information about the physical location(s) of the boundaries of the trackpad. For example, the medical electronic device may record information about the location of the perimeter of the trackpad. Having defined the location of the trackpad, the medical electronic device may define (at operation 902), operations that are associated with movements in a first direction on the trackpad and operations that are associated with movements in a second direction on the trackpad. The second direction is orthogonal to the first direction. That is, the medical electronic device may define the direction of movements of the tracked pointer along the trackpad that will be considered to be a movement in an x direction and the direction of movements of the tracked pointer along the trackpad that will be considered to be a movement in a y direction.

Then, at operation 906, the medical electronic device determines whether the present location of the pointer tool indicates activation of the trackpad. For example, the medical electronic device may determine whether the present location of the pointer tool associated with the tracking markers to the location, in space, of the trackpad. At operation 908, if the location of the pointer tool indicates activation of the trackpad, the medical electronic device translates a direction of movement along the virtual trackpad into x and y components and, at operation 910, the operating state of the medical electronic device may be adjustment based on the x and y components. For example, in one embodiment, a user interface of the medical electronic device may be updated so that a cursor displayed on the user interface is moved in accordance with the x and y components.

As generally described above, in some embodiments, the location of a virtual interface element may be defined during a calibration mode by moving a tracked pointer tool to one or more locations which define the location(s) of the interface element. In other embodiments, which will be discussed in greater detail below, a tracked interface element fixture may be used to obviate or reduce the need for calibration. As will be understood from the following description, the fixture can also assist in environments in which the optical tracking system may move relative to the interface element. For example, if a camera associated with the optical tracking system is movable, the system may lose calibration of the virtual interface elements each time the camera is moved. However, by relying upon a tracked fixture of the type described below, the virtual interface elements may remain calibrated even after movement of the camera. It should be noted that in some embodiments this tracked fixture may also function as a patient reference (as is commonly used in the art). It should also be noted that all of the virtual interface elements described in use with a tracked fixture as described below may also be used independently of the tracked fixtures, having their positions defined in space to the tracking device by the user.

Figures 10A, 10B:
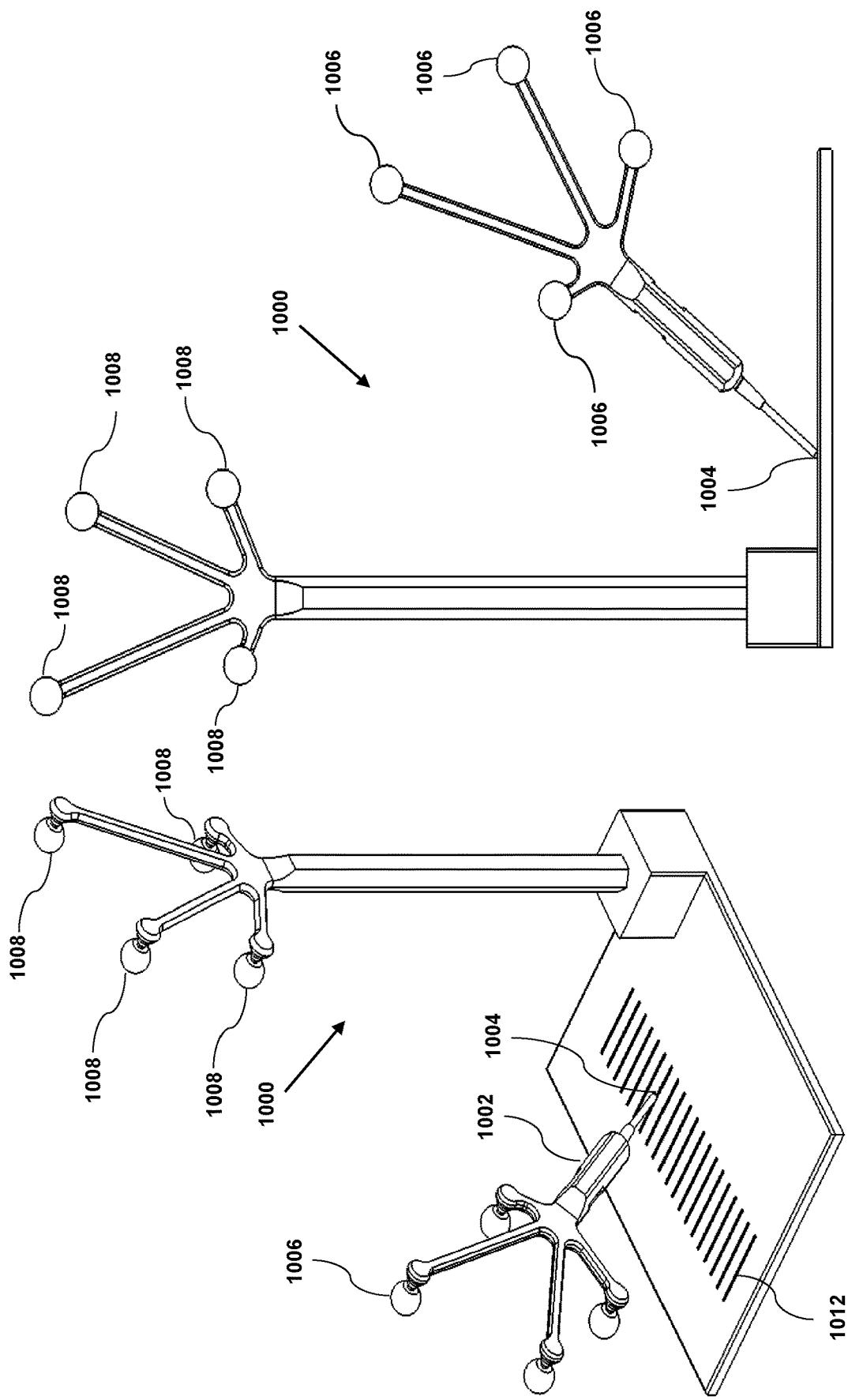
FIG. 10A is a perspective view of an embodiment of a fixture that provides a virtual interface element and a pointer tool engaging the virtual interface element.
FIG. 10B is a front elevation view of the fixture and pointer tool of FIG. 10A.

Referring now to FIGS. 10A and 10B, a tracked interface element fixture 1000 is illustrated. The fixture 1000 includes a three or more fixed tracking markers 1008 which are fixedly mounted to the fixture 1000. In the example illustrated, there are four fixed tracking markers 1008. The fixture 1000 also includes an interface element 1012 which is identified on the fixture 1000 by one or more visual indicators and which is maintained at a constant distance from the fixed tracking markers 1008. That is, the interface element 1012 does not move relative to the fixed tracking markers 1008. The visual indicator may be a printing, line, marking, depression, cavity or groove which indicate a location of the interface element 1012.

An operator may interact with the interface element 1012 by moving a tracked pointing tool 1002 so that the tip 1004 of the tracked pointing tool 1002 is in a location associated with the interface element 1012.

The fixed tracking markers 1008 are arranged in a pattern that is unique to the fixture 1000. That is, tracked medical instruments such as a tracked pointer tool 1002 which may be used to activate the interface element, have a different arrangement of tracking markers 1006 than the arrangement of the fixed tracking markers. This uniqueness allows the medical electronic device to identify the fixture 1000. For example, in operation 902 of the method 900, the medical electronic device may identify the fixture using identification information stored in memory of the medical electronic device. For example, at operation 902, the medical electronic device may determine that the fixture 1000 is available (i.e., that it has been detected by the optical tracking system) and that the interface element 1012 is, therefore, available to be activated by an operator. The medical electronic device is configured with information that indicates the location of the interface element 1012 on the fixture relative to the fixed tracking markers 1008. Thus, by identifying the fixed tracking markers 1008, the medical electronic device then determines the location, in space, of the interface element 1012.

Once the interface element is located using the fixed tracking markers 1008, the medical electronic device can then detect whether it has been activated and the nature of the activation. For example, at operation 906, the medical electronic device may determine whether the tracked pointer tool 1002 has been moved to a location associated with the interface element. If the interface element 1012 is determined to have been activated, at operation 908, the medical electronic device may determine that an input command has been received. The nature of the input command that is determined to have been received may depend on the nature of the activation of the interface element. For example, as was described above, the direction of the activation may be considered by the medical electronic device. For example, movement along the interface element in a first direction may be associated with a first input command while movement in a second direction may be associated with a second input command. As with the embodiments discussed above, dwell time and volumetric threshold parameters may be used by the medical electronic device when determining whether an interface element has been activated.

While FIGS. 10A and 10B illustrate an interface element which is a virtual slider, other types of interface elements may be provided on the fixture in other embodiments. For example, a virtual button, virtual dial, or virtual trackpad may be provided in other embodiments.

In at least some embodiments, when the fixture 1000 is moved, the medical electronic device automatically re-determines the location, in space, of the interface element. Thus, activation of the interface element may be detected even when the interface element is moved to a new location.

Although the embodiments above include both a fixture and interface element in some embodiments the interface element may be implemented without the use of the fixture and more specifically without the fixed tracking markers. In such a scenario the location of the interface element may be communicated to the system by indicating the location of the interface component (for example, interface element 1012 without the tracking markers 1008) by placing the pointer tool on the boundaries of the interface and indicating to the system which interface's location is being defined. For example, the pointer could indicate the position of the corners of the interface element 1012 to the system using the pointer tool so the system would know its location in the surgical space without the need for the tracking markers 1008. This may be advantageous in some scenarios where the interface component need not be moved, thus saving space by alleviating the need for the tracking markers 1008 and their associated mounting assembly. That being said however the interface element 1012 with associated tracking markers 1008 does have an advantage in some scenarios as they allow for the dynamic movement of the interface element in the surgical space without having to redefine the position of the interface to the system such as in the example provided above.

Figure 11B:
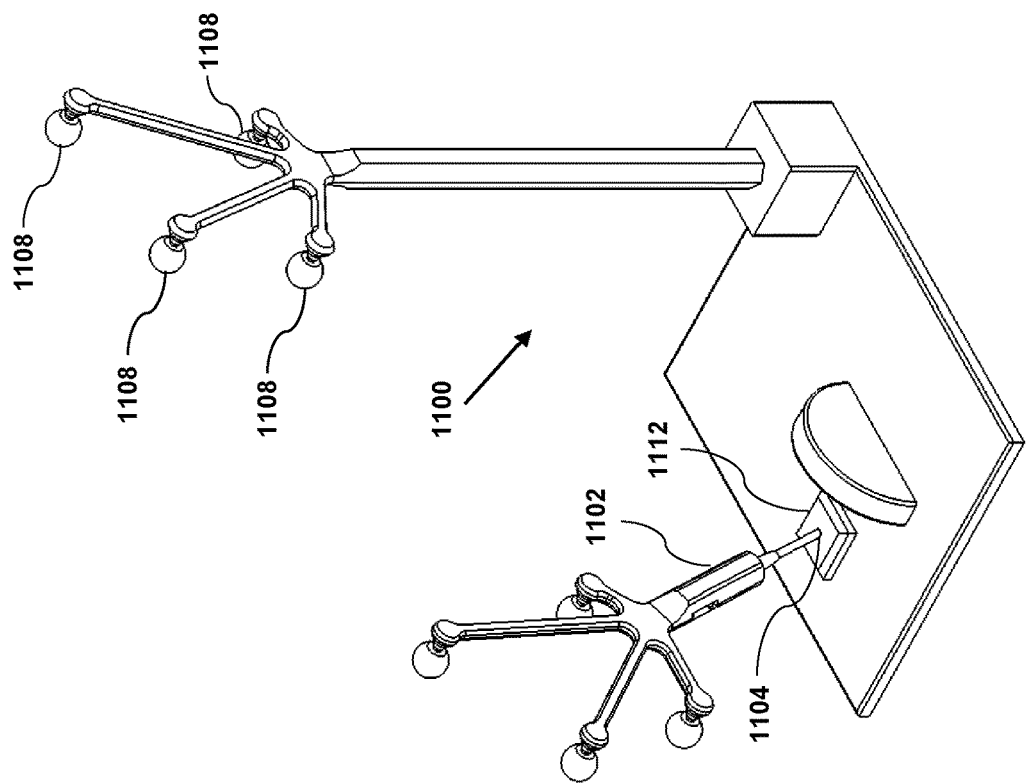
FIG. 11B is a rear perspective view of the fixture and the pointer tool of FIG. 11A.
Figure 11A:
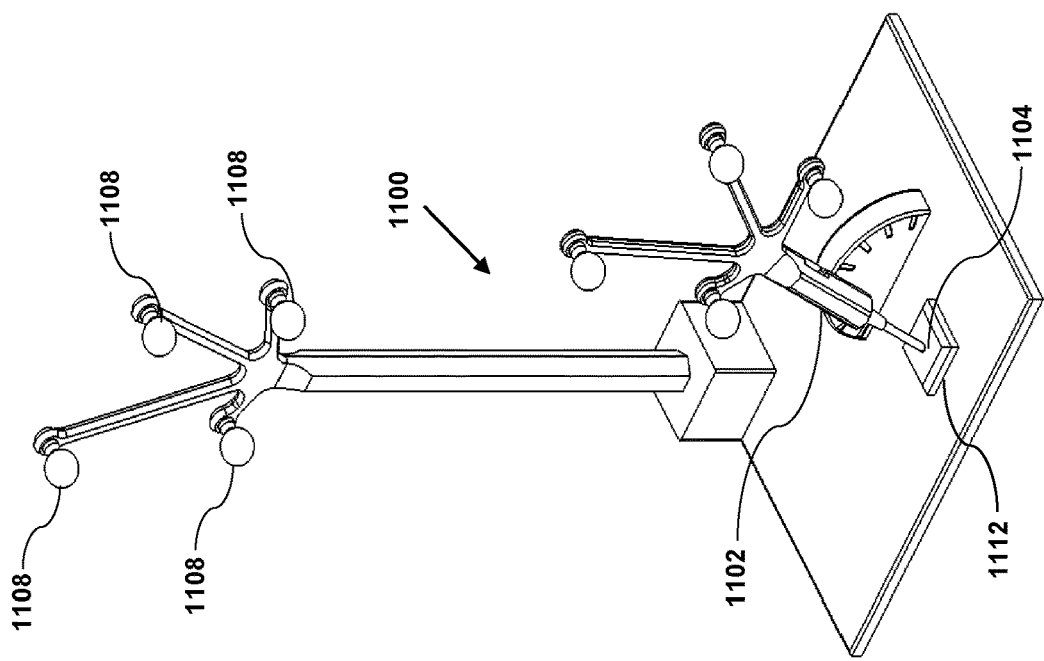
FIG. 11A is a front perspective view of an embodiment of a fixture that provides a joystick-type virtual interface element and a pointer tool engaging the virtual interface element.
Figure 13C:
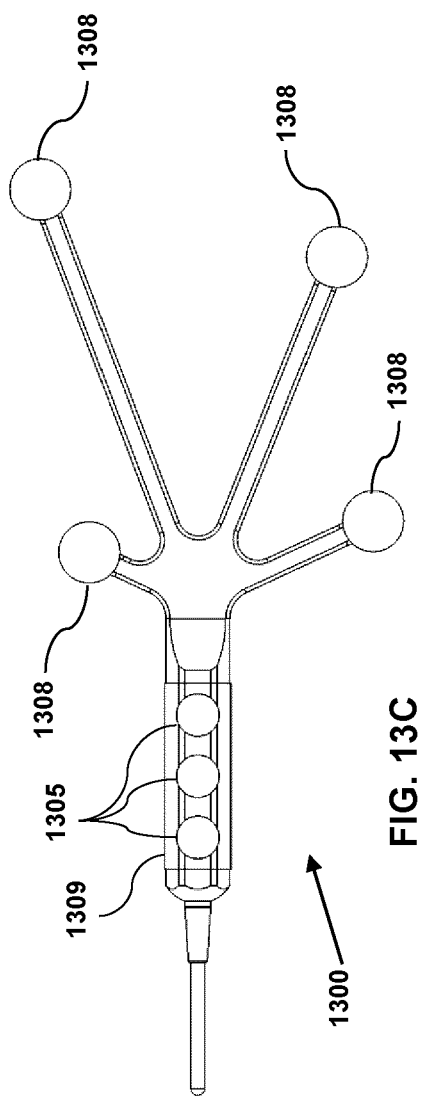
FIG. 13C is a top view of the tracked pointer tool of FIG. 13B.
Figure 13D:
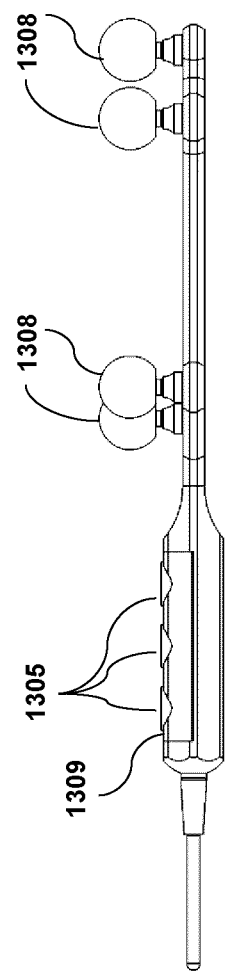
FIG. 13D is a side view of the tracked pointer tool of FIG. 13B.
Figure 13E:
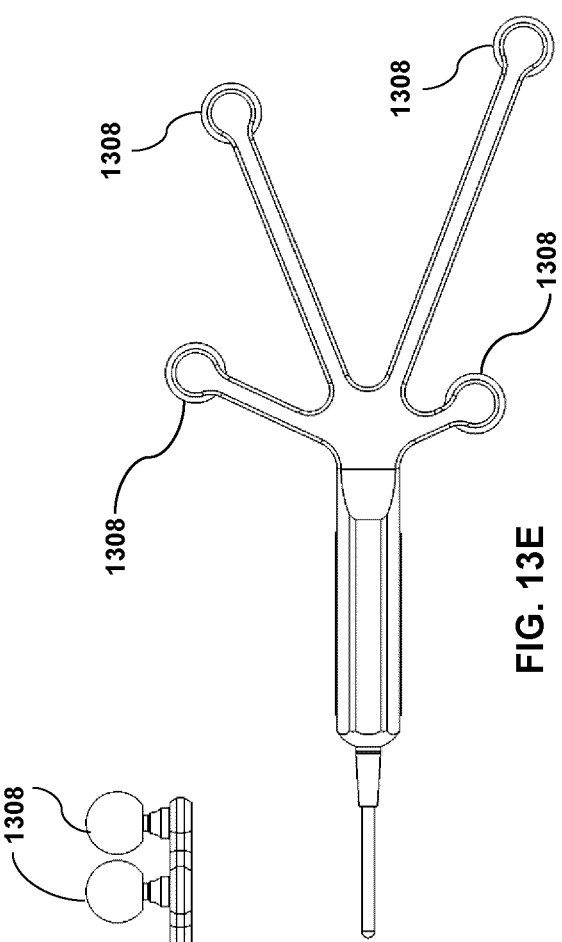
FIG. 13E is a bottom view of the tracked pointer tool of FIG. 13B.

Reference will now be made to FIGS. 11A and 11B which illustrate a further fixture 1100 which may be used with the medical electronic device. The fixture 1100 of FIGS. 11A and 11B is similar to the fixture 1000 of FIGS. 10A and 10B in that it includes three or more fixed tracking markers 1108 and a visual indicator that indicates the location of an interface element 1112. Much like the fixture 1000 of FIGS. 10A and 10B, the fixture 1100 of FIGS. 11A and 11B is configured to be activated by a tracked pointer tool 1102. The interface element 1112 is located at a fixed position relative to the fixed tracking markers 1108. The interface element 1112 in FIGS. 11A and 11B is a point that is visually indicated by a divot, slot, or point that the tip 1104 of the pointer tool 1102 is configured to engage. For example, the tip 1104 may be inserted within a slot located at the interface element.

As with the fixture 1000 of FIGS. 10A and 10B, the medical electronic device is configured to recognize the fixture 1100 of FIGS. 11A and 11B based on the pattern of the fixed tracking markers 1108. That is, the tracking markers 1108 are arranged in a pattern that is unique to the fixture (i.e., are different from fixtures of other types or from the pattern of tracking markers on the pointer tool). In recognizing the fixture 1100, the medical electronic device also identifies (at operation 902) the location, in space, of the interface element (i.e., based on the location of the fixed tracking markers). Then, the medical electronic device may determine (at operation 906) whether a present location of the tracked pointer tool indicates that the interface element has been activated.

The fixture 1100 of FIGS. 11A and 11B provides a virtual joystick. More particularly, the interface element 1112 may be activated by placing the pointer tool in the location associated with the interface and then the angular orientation of the pointer tool may be varied by an operator to change an input command that is issued to the medical electronic device. Thus, in at least some embodiments, the medical electronic device determines (at operation 908), an angular orientation of the pointer tool. In some embodiments, this may involve determining whether the pointer tool is angled in a left-of-center orientation or determining whether the pointer tool is angled in a right-of-center orientation. The medical electronic device may associate a separate input command with a left-of-center orientation than with a right-of-center orientation. For example, a right-of-center orientation may increase a parameter while a left-of-center orientation may decrease the parameter. By way of example, the parameter may control a volume, a zoom level, a position of a robotic arm, etc.

Reference will now be made to FIGS. 12A-12F which illustrate a pointer tool 1200 which includes one or more fixed tracking markers 1208 and one or more movable tracking markers 1210 that are movable relative to the fixed tracking markers 1208. For example, in one embodiment, the pointer tool includes three or more fixed tracking markers 1208 and one movable tracking marker 1210. In the illustrated embodiment, four fixed tracking markers 1208 are included and one movable tracking marker 1210. These tracking markers are provided on a pointer tool 1200 having a tip 1202 that may be used for pointing.

The fixed tracking markers 1208 are fixedly mounted relative to one another and the movable tracking marker is movable relative to the fixed tracking markers. That is, the movable tracking marker is movably coupled to the fixed tracking markers. In the example, the movable tracking marker is rotatable. More particularly, the movable tracking marker 1210 is mounted on an arm that rotably connects to a frame that supports the fixed tracking markers 1208. The movable tracking marker can, however, be movable in a different manner in other embodiments. For example, the movable tracking marker may be slidable relative to the fixed tracking markers in some embodiments.

In at least some embodiments, an operator may move the movable tracking marker in order to input an input command to the medical electronic device. That is, the orientation of the movable tracking marker relative to the orientation of the fixed tracking markers may be varied in order to issue an input command. For example, at operation 902 of the method 900 of FIG. 9, a first input command is defined by assigning a first orientation of the movable tracking marker to a first operating mode of the medical electronic device. The first orientation is an orientation relative to the fixed tracking markers. In some embodiments, a second input command may also be defined by assigning a second orientation of the movable tracking marker to a second operating mode of the medical electronic device.

At operation 904, the medical electronic device identifies the present orientation of the movable tracking marker relative to the fixed tracking markers. This present orientation is then used to determine, at operation 908, whether an input command has been received. For example, if the present orientation is the first orientation, then the medical electronic device determines that the first input command is received and, at operation 910, the operating state is adjusted accordingly. If, the present orientation is the second orientation, then the medical electronic device determines that the second input command is received and, at operation 910, the operating state is adjusted accordingly.

Referring now to FIGS. 13A to 13E, an example of a pointer tool 1300 having a plurality of coverable tracking markers 1305 is illustrated. The coverable tracking markers 1305 are sized and positioned to be coverable by an operator's finger. In the example illustrated, the coverable tracking markers are finger-sized pads and are located on a handle that is configured to be gripped by a user's hand. More particularly, in the illustrated embodiment, these pads are located on a cartridge 1309 that removably attaches to the pointer tool 1300 at the handle. Since the cartridge is removable, the pads can be easily replaced. Which in some cases provides a way to refresh the pads if for example they are stained or covered with bodily fluids, or any substance in the operating space that may hinder their detection by the tracking system.

The coverable tracking markers 1305 are, in some embodiments, reflective tape or pads. In the illustrated embodiment, there are three pads which are all arranged in a single column longitudinally along the handle of the pointer tool. As will be explained in greater detail below, this orientation and configuration may be useful to provide a two-stage trigger. In embodiments where the coverable tracking markers are in the form of a length of tape or more generically an elongated reflective strip the strip may act as a variable switch. For example, the switch may be formed of coverable portions that allow for an operator to variably adjust the degree to which an option is selected. For example, the switch may control a contrast option on the user interface of the medical electronic device.

The pointer tool 1300 includes other tracking markers 1308 apart from the coverable tracking markers. In the illustrated embodiment, these other tracking markers 1308 are spheres.

In at least some embodiments, at operation 902 of the method 900 of FIG. 9, a two-stage trigger is defined. More particularly, a "primed" input command (which may also be referred to as a priming command) is defined. The system may be configured to await the primed input command. In some embodiments, the primed input command is defined to associate a first covered state of the coverable tracking markers 1305 with a "primed" operating state of the medical electronic device. The priming command is a command to prime the system or medical device for receiving a trigger input command. A "trigger" input command (which may be referred to simply as an input command) is defined to associate a second covered state of the coverable tracking markers 1305 with a "trigger" operating state of the medical electronic device. The first operating state may be a state in which a first one of the coverable tracking markers 1305 is covered but a second one of the coverable tracking markers and a third one of the tracking markers are not covered. For example, the first operating state may exist when the middle coverable tracking marker is covered but the top and bottom coverable tracking markers are exposed.

The second operating state may be a state in which a second one of the coverable tracking markers is covered along with the first one of the coverable tracking markers. For example, the second one of the tracking markers may be the top coverable tracking marker.

The two stage trigger requires an operator to issue two different input commands, in sequence, before the desired operation is performed.

After the two stages of the trigger are defined at operation 902, the medical electronic device monitors the tracking markers to identify the present state of the tracking markers at operation 904. In at least some embodiments, the medical electronic device is only configured to begin monitoring for the first covered state (i.e., the state associated with the "primed" input command) after the medical electronic device detects that the coverable tracking markers are in a "normal" state in which the coverable tracking markers are not covered. When this normal state is detected, the medical electronic device continues to identify the present state of the coverable tracking markers to determine whether any of the coverable tracking markers become covered. If the coverable markers become covered, the medical electronic device compares the present state of the coverable tracking markers to the first covered state at operation 906 (i.e., the state associated with the "primed" input command). If the present state is the same as the first covered state, then the medical electronic device determines that a "primed" input command has been received at operation 908 and initiates a "primed" operating mode at operation 910 in which it begins to monitor for the second covered state (i.e., the state associated with the trigger input. If the second covered state is observed, then the medical electronic device enters the "trigger" operating state.

The medical electronic device may be configured to store, in memory, the current operating state. For example, a value representing the current operating state may be stored in memory.

The "trigger" operating state may, for example, cause a robotic arm to be moved.

Generally, a computer, computer system, computing device, client or server, as will be well understood by a person skilled in the art, includes one or more than one electronic computer processor, and may include separate memory, and one or more input and/or output (I/O) devices (or peripherals) that are in electronic communication with the one or more processor(s). The electronic communication may be facilitated by, for example, one or more busses, or other wired or wireless connections. In the case of multiple processors, the processors may be tightly coupled, e.g. by high-speed busses, or loosely coupled, e.g. by being connected by a wide-area network.

A computer processor, or just "processor", is a hardware device for performing digital computations. It is the express intent of the inventors that a "processor" does not include a human; rather it is limited to be an electronic device, or devices, that perform digital computations. A programmable processor is adapted to execute software, which is typically stored in a computer-readable memory. Processors are generally semiconductor based microprocessors, in the form of microchips or chip sets. Processors may alternatively be completely implemented in hardware, with hard-wired functionality, or in a hybrid device, such as field-programmable gate arrays or programmable logic arrays. Processors may be general-purpose or special-purpose off-the-shelf commercial products, or customized application-specific integrated circuits (ASICs). Unless otherwise stated, or required in the context, any reference to software running on a programmable processor shall be understood to include purpose-built hardware that implements all the stated software functions completely in hardware.

Multiple computers (also referred to as computer systems, computing devices, clients and servers) may be networked via a computer network, which may also be referred to as an electronic network or an electronic communications network. When they are relatively close together the network may be a local area network (LAN), for example, using Ethernet. When they are remotely located, the network may be a wide area network (WAN), such as the internet, that computers may connect to via a modem, or they may connect to through a LAN that they are directly connected to.

Computer-readable memory, which may also be referred to as a computer-readable medium or a computer-readable storage medium, which terms have identical (equivalent) meanings herein, can include any one or a combination of non-transitory, tangible memory elements, such as random access memory (RAM), which may be DRAM, SRAM, SDRAM, etc., and nonvolatile memory elements, such as a ROM, PROM, FPROM, OTP NVM, EPROM, EEPROM, hard disk drive, solid state disk, magnetic tape, CDROM, DVD, etc.) Memory may employ electronic, magnetic, optical, and/or other technologies, but excludes transitory propagating signals so that all references to computer-readable memory exclude transitory propagating signals. Memory may be distributed such that at least two components are remote from one another, but are still all accessible by one or more processors. A nonvolatile computer-readable memory refers to a computer-readable memory (and equivalent terms) that can retain information stored in the memory when it is not powered. A computer-readable memory is a physical, tangible object that is a composition of matter. The storage of data, which may be computer instructions, or software, in a computer-readable memory physically transforms that computer-readable memory by physically modifying it to store the data or software that can later be read and used to cause a processor to perform the functions specified by the software or to otherwise make the data available for use by the processor. In the case of software, the executable instructions are thereby tangibly embodied on the computer-readable memory. It is the express intent of the inventor that in any claim to a computer-readable memory, the computer-readable memory, being a physical object that has been transformed to record the elements recited as being stored thereon, is an essential element of the claim.

Software may include one or more separate computer programs configured to provide a sequence, or a plurality of sequences, of instructions to one or more processors to cause the processors to perform computations, control other devices, receive input, send output, etc.

It is intended that the invention includes computer-readable memory containing any or all of the software described herein. In particular, the invention includes such software stored on non-volatile computer-readable memory that may be used to distribute or sell embodiments of the invention or parts thereof.

Where, in this document, a list of one or more items is prefaced by the expression "such as" or "including", is followed by the abbreviation "etc.", or is prefaced or followed by the expression "for example", or "e.g.", this is done to expressly convey and emphasize that the list is not exhaustive, irrespective of the length of the list. The absence of such an expression, or another similar expression, is in no way intended to imply that a list is exhaustive. Unless otherwise expressly stated or clearly implied, such lists shall be read to include all comparable or equivalent variations of the listed item(s), and alternatives to the item(s), in the list that a skilled person would understand would be suitable for the purpose that the one or more items are listed.

The specific embodiments described above have been shown by way of example, and it should be understood that these embodiments may be susceptible to various modifications and alternative forms. It should be further understood that the claims are not intended to be limited to the particular forms disclosed, but rather to cover modifications, equivalents, and alternatives falling within the spirit and scope of this disclosure.

We claim:

1. A system, the system comprising:
a processor programmed with instructions which, when executed, configure the processor to:
configure an input command by assigning at least one operating state of a medical electronic device to a particular state of at least one tracking marker of at least three tracking markers detectable by an optical tracking system, the at least three tracking markers fixedly disposed in relation to a fixture, the at least three tracking markers comprising at least three finger-sized pads, the at least three finger-sized pads coverable, the at least three tracking markers disposed on a cartridge, and the cartridge removably coupled with a handle of a pointer tool, whereby at least one assigned operating state is provided;
await receiving a priming command from a user, the priming command being a command to prime the system for receiving the input command;
after receiving the priming command, identify a present state of the at least three tracking markers based on data from the optical tracking system;
compare the present state with the particular state assigned to the at least one operating state, whereby a comparison is provided;
based on the comparison, determine whether an input command is received by determining whether a tracked medical instrument is disposed in a location associated with a virtual interface element, the virtual interface element comprising one of a virtual scroll bar, a virtual slider, a virtual button, a virtual dial, and a virtual trackpad; and if the input command is received, adjust the at least one operating state of the medical electronic device to the at least one assigned operating state, the at least one operating state comprising at least one of a mode, a function, and an operation, and the input command comprising at least one of a selection command, a modification command, and set command in relation to a parameter value, wherein the medical electronic device is operable by way of a plurality of triggers, in sequence, before performing a certain operation, wherein the plurality of triggers comprises the priming command and the input command, and wherein the input command is distinct relative to the priming input command.

2. The system of claim 1, wherein the processor is further configured to determine whether the input command is received, based on the comparison, by determining whether a location of the at least one tracking marker of the at least three tracking markers indicates a physical location assigned to the at least one operating state, and wherein, if the location of the at least one tracking marker of the at least three tracking markers indicates the physical location assigned to the at least one operating state, the particular state of the at least one tracking marker of the at least three tracking markers comprises the physical location assigned to the at least one operating state.

3. The system of claim 1, wherein the processor is further configured to determine whether the input command is received by determining whether at least one tracking marker of the at least three tracking markers is covered based on the comparison, and wherein, if at least one tracking marker of the at least three tracking markers is covered based on the comparison, the particular state of the at least one tracking marker of the at least three tracking markers comprises a covered state.

4. The system of claim 1, wherein the processor is further configured to update a memory to reflect a primed operating state when the priming command is received, and wherein the certain operation comprises repositioning a robotic arm.

5. The system of claim 1, wherein, if the virtual interface element comprises the virtual button, the processor is further configured to configure the input command by assigning the at least one operating state to a location of the virtual button, the present state comprises a present location of a pointer tool associated with the at least three tracking markers, and the processor is further configured to compare the present location of the at least three tracking markers with the location of the virtual button to determine whether the present location of the at least three tracking marker indicates activation of the virtual button.

6. The system of claim 5, wherein the processor is further configured to determine whether the input command is received by determining whether the virtual button is activated for at least a minimum dwell time based on the comparison.

7. The system of claim 1, wherein, if the virtual interface element comprises the virtual dial, the processor is further configured to configure the input command by defining a path of the virtual dial, wherein the present state comprises a present location of a pointer tool associated with the at least three tracking markers, and wherein the processor is further configured to compare the present location of the pointer tool with the path of the virtual dial to determine whether the present location of the at least one tracking marker indicates activation of the virtual dial.

8. The system of claim 1, wherein the processor is further configured to configure the input command by defining a path between terminal points, wherein the present state comprises a present location of a pointer tool associated with the at least three tracking markers, and wherein the processor is further configured to compare the present location of the pointer tool with the path.

9. The system of claim 1, wherein, if the virtual interface element comprises the virtual trackpad, the processor is further configured to configure the input command by defining the virtual trackpad, wherein the present state comprises a present location of a pointer tool associated with the at least three tracking markers, and wherein the processor is further configured to compare the present location of the pointer tool with a location of the virtual trackpad.

10. The system of claim 1, wherein the processor is further configured to configure the input command by determining a location of the interface element based on a location of the at least three tracking markers, and wherein the fixture comprises a visual indicator to indicate the location of the interface element.

11. The system of claim 1, wherein the at least three tracking markers comprise at least three further fixed tracking markers and at least one movable tracking marker, each fixed tracking marker of the at least three further fixed tracking markers fixedly mounted relative to another fixed tracking marker of the at least three further fixed tracking markers, and the movable tracking marker movable relative to the at least three further fixed tracking markers, wherein the tracked medical instrument is fixedly disposed relative to the at least three further fixed tracking markers, and wherein the processor is further configured to, after receiving the priming command, identify a present orientation of the at least one movable tracking marker relative to the at least three further fixed tracking markers.

12. A method performed by way of a system comprising a processor, the method comprising:

using the processor, configuring an input command by assigning at least one operating state of a medical electronic device to a particular state of at least one tracking marker of at least three tracking markers detectable by an optical tracking system, the at least three tracking markers fixedly disposed in relation to a fixture, the at least three tracking markers comprising at least three finger-sized pads, the at least three finger-sized pads coverable, the at least three tracking markers disposed on a cartridge, and the cartridge removably coupled with a handle of a pointer tool, thereby providing at least one assigned operating state;

awaiting receiving a priming command, the priming command comprising a command to prime the medical electronic device for receiving the input command;

after receiving the priming command, identifying a present state of the at least three tracking markers based on data from the optical tracking system;

comparing the present state with the particular state assigned to the at least one operating state, thereby providing a comparison;

based on the comparison, determining whether the input command is received by determining whether a tracked medical instrument is disposed in a location associated with a virtual interface element, the virtual interface element comprising one of a virtual scroll bar, a virtual slider, a virtual button, a virtual dial, and a virtual trackpad, and the location of the interface element assigned during a calibration routine; and if the input command is received, adjusting the at least one operating state of the medical electronic device to the at least one assigned operating state, the at least one operating state comprising at least one of a mode, a function, and an operation, and the input command comprising at least one of a selection command, a modification command, and set command in relation to a parameter value, wherein the medical electronic device is operable by way of a plurality of triggers, in sequence, before performing a certain operation, wherein the plurality of triggers comprises the priming command and the input command, and wherein the input command is distinct relative to the priming input command.

13. The method of claim 12, wherein determining whether the input command is received comprises determining whether a location of at least one tracking marker of the at least three tracking markers indicates a physical location assigned to the at least one operating state, and wherein, if the location of the at least one tracking marker of the at least three tracking markers indicates the physical location assigned to the at least one operating state, the particular state of the at least one tracking marker of the at least three tracking markers comprises the physical location assigned to the at least one operating state.

14. The method of claim 12, wherein determining whether the input command is received comprises determining whether at least one tracking marker of the at least three tracking markers is covered, and wherein, if at least one tracking marker of the at least three tracking markers is covered based on the comparison, the particular state of the at least one tracking marker of the at least three tracking markers comprises a covered state.

15. The method of claim 12, further comprising updating a memory to reflect a primed operating state when the priming command is received, wherein the certain operation comprises repositioning a robotic arm.

16. The method of claim 12, wherein, if the virtual interface element comprises the virtual button, in determining whether the input command is received, configuring the input command further comprises assigning the operating state to a location of the virtual button, in identifying the present state, the present state comprises a present location of a pointer tool associated with the at least three tracking markers, and comparing comprises comparing a present location of the at least three tracking markers with the location of the virtual button to determine whether the present location of the tracking marker indicates activation of the virtual button.

17. The method of claim 16, wherein determining whether the input command is received comprises determining whether the virtual button is activated for at least a minimum dwell time.

18. The method of claim 12, wherein, if the virtual interface element comprises the virtual dial, in determining whether the input command is received, configuring the input command further comprises defining a path of the virtual dial, in identifying the present state, the present state comprises a present location of a pointer tool associated with the at least three tracking markers, and comparing comprises comparing the present location of the pointer tool with the path of the virtual dial to determine whether the present location of the at least one tracking marker indicates activation of the virtual dial.

19. The method of claim 12, wherein configuring the input command further comprises defining a path between terminal points, wherein, in identifying the present state, the present state comprises a present location of a pointer tool associated with the at least three tracking markers, and wherein comparing comprises comparing the present location of the pointer tool with the path.

20. A non-transitory processor-readable storage medium comprising processor-executable instructions which, when executed, configure a processor to:

configure an input command by assigning at least one operating state of a medical electronic device to a particular state of at least one tracking marker of at least three tracking markers detectable by an optical tracking system configured to detect at least three tracking markers fixedly, the at least three tracking markers fixedly disposed in relation to a fixture, the at least three tracking markers comprising at least three finger-sized pads, the at least three finger-sized pads coverable, the at least three tracking markers disposed on a cartridge, and the cartridge removably coupled with a handle of a pointer tool, whereby at least one assigned operating state is provided;

await receiving a priming command from a user, the priming command comprising a command to prime the medical electronic device for receiving the input command;

after receiving the priming command, identify a present state of the at least three tracking markers based on data from the optical tracking system;

compare the present state with the particular state assigned to the at least one operating state, whereby a comparison is provided;

based on the comparison, determine whether the input command is received by determining whether a tracked medical instrument is disposed in a location associated with a virtual interface element, the virtual interface element comprising one of a virtual scroll bar, a virtual slider, a virtual button, a virtual dial, and a virtual trackpad, and the location of the interface element assigned during a calibration mode; and if the input command is received, adjust the operating state of the medical electronic device to the at least one assigned operating state, the operating state comprising at least one of a mode, a function, and an operation, and the input command comprising at least one of a selection command, a modification command, and set command in relation to a parameter value, wherein the medical electronic device is operable by way of a plurality of triggers, in sequence, before performing a certain operation, wherein the plurality of triggers comprises the priming command and the input command, and wherein the input command is distinct relative to the priming input command.

* * * * *